United States Patent [19]

Potter et al.

[11] Patent Number: 4,733,354

[45] Date of Patent: Mar. 22, 1988

[54] METHOD AND APPARATUS FOR AUTOMATED MEDICAL DIAGNOSIS USING DECISION TREE ANALYSIS

[75] Inventors: Brian Potter, 3305 Pottawattamie Trail, Michigan City, Ind. 46360; Michael C. Potter, Spring Valley, Calif.

[73] Assignee: Brian Potter, Michigan City, Ind.

[21] Appl. No.: 674,130

[22] Filed: Nov. 23, 1984

[51] Int. Cl.⁴ .............................................. C06F 15/42
[52] U.S. Cl. ..................................... 364/415; 128/630
[58] Field of Search ....................... 364/415; 128/630; 379/70, 92, 128; 358/342

[56] References Cited

U.S. PATENT DOCUMENTS

| | | | |
|---|---|---|---|
| 3,566,370 | 6/1969 | Worthington et al. | 128/906 |
| 3,794,982 | 2/1974 | McCormick et al. | 364/900 |
| 3,829,844 | 8/1974 | Zonneveld et al. | 364/900 |
| 3,970,996 | 7/1976 | Yasaka et al. | 364/200 |
| 4,130,881 | 12/1978 | Haessler et al. | 364/415 |
| 4,290,114 | 9/1981 | Sinay | 364/415 |
| 4,315,309 | 2/1982 | Coli | 364/200 |
| 4,489,387 | 12/1984 | Lamb | 128/630 |

OTHER PUBLICATIONS

Readings in Medical Artificial Intelligence, William J. Clancey; Edward H. Shortliffe.
"Computer-Assisted Clinical Decision Making"; Methods of Information in Medicine, 12:45-51 (1973); G. Anthony Gorry.
Data Base: Structured Techniques for Design, Performance and Management, S. Atre, pp. 248-251, 99-104 (1980).
Standard Pascal: User Reference Manual, Doug Cooper, pp. 137-141 (1983).
"Dermatopathology Symposium" by the New York University Post-Graduate Medical School given Oct. 13-15, 1977, (selected pages).

Primary Examiner—Jerry Smith
Assistant Examiner—Gail D. Hayes
Attorney, Agent, or Firm—Larson and Taylor

[57] ABSTRACT

An interactive method for performing a differential medical diagnosis utilizing a programmed computer system and a stored data base. In one particular embodiment, the method is for making a dermatopathological diagnosis based on operator selections from data files sequentially presented from the broadest scope to the narrowest scope. The data base is stored in a forwardly and backwardly linked hierarchical array of data files. If the data base were graphically arranged according to the linkages, it would appear in the form of a decision tree having a plurality of levels, each level encompassing the entire subject matter of dermatopathology. Each data file in the data base corresponds to a node of the decision tree and the records in the data file correspond to the branches.

13 Claims, 16 Drawing Figures

```
PRESS
  0    TO GO BACK
  1    EPIDERMAL
  2    DERMAL
  3    SUBCUTANEOUS
  4    TO MODIFY

CHOICE
  2
```

FIG. 7a

```
PRESS
  0    TO GO BACK
  1    EPITHELIAL PROLIFERATION
  2    VESICULATION
  3    INFILTRATION
  4    PHAGOCYTOSIS OF PIGMENT
  5    COLLAGENOUS PROLIFERATION
  6    ELASTOSIS
  7    VASCULAR CHANGES
  8    ATROPHY
  9    TO MODIFY

CHOICE
  3
```

FIG. 7b

```
PRESS
  0    TO GO BACK
  1    LEUCOCYTIC
  2    CELLULAR NONCOLLAGENOUS
  3    EXTRACELLULAR ACCUMULATION
  4    INCREASED AMOUNTS OF MUCIN
  5    PIGMENTED CELLS
  6    CELLS WITH FOAMY CYTOPLASM
  7    CELLULAR NESTS
  8    CELLULAR AND COLLAGENOUS
  9    TO MODIFY

CHOICE
  3
```

FIG. 7c

```
PRESS
  0    TO GO BACK
  1    SMALL EOSINOPHILIC GLOBULES
  2    CLEFTED BASOPHILIC DEPOSITS
  3    BASOPHILIC ELASTOTIC FIBERS
  4    SPICULE OF OSSIFIED BONE
  5    TO MODIFY

CHOICE
  1
```

FIG. 7d

```
PRESS
  0    TO GO BACK
  1    CUTANEOUS AMYLOIDOSIS
  2    COLLOID MILIUM
  3    ACTINIC ELASTOSIS
  4    OSTEOMA CUTIS
  5    TO MODIFY

MOST LIKELY DIAGNOSIS 1
```

FIG. 7e

```
FILE 1          ANTECEDENT 1
2  EPIDERMAL
3  DERMAL
4  SUBCUTANEOUS
```

*FIG. 8a*

```
FILE 3          ANTECEDENT 1
10  EPITHELIAL HYPERPLASIA
11  VESICULATION
12  INFILTRATION
13  CELLULAR NESTS
14  FIBROSIS
15  ELASTOSIS
16  VASCULAR CHANGES
17  ATROPHY
```

*FIG. 8b*

```
FILE 12         ANTECEDENT 3
53  LEUCOCYTIC
54  CELLULAR
55  EXTRACELLULAR ACCUMULATION
56  INCREASED AMTS. OF MUCIN
```

*FIG. 8c*

```
FILE 55         ANTECEDENT 12
1631  SMALL EOSINOPHILIC GLOBULES
1632  CLEFTED BASOPHILIC DEPOSITS
1633  BASOPHILIC ELASTOTIC FIBERS
1634  SPICULE OF OSSIFIED BONE
```

*FIG. 8d*

```
FILE 163        ANTECEDENT 55
CUTANEOUS AMYLOIDOSIS
COLLOID MILIUM
ACTINIC ELASTOSIS
OSTEOMA CUTIS
```

*FIG. 8e*

METHOD AND APPARATUS FOR AUTOMATED MEDICAL DIAGNOSIS USING DECISION TREE ANALYSIS

FIELD OF THE INVENTION

The present invention relates in general to an automated or computerized diagnosic system and technique for diagnosising a medical condition. In one particular embodiment, the present invention relates to a dermatopathological diagnosis based on observations of a biopsy and the selection of one option from among a set of sequentially presented options called from a forwardly linked data base.

BACKGROUND OF THE INVENTION

In the medical field in particular, there is a need for automating a diagnosis of a medical condition based on certain observations, test results and characteristics of the patient. For example, many medical diagnoses are made based on information obtained from examination of the patient, including diagnostic tests, and based on information received directly from the patient.

Computerized diagnostic systems are known and are the subject of many patents, for example: U.S. Pat. Nos. to Sinay 4,290,114 and to Coli 4,315,309. In addition, other U.S. patents disclose computerized systems for obtaining medical information, for example: U.S. Pat. Nos. to Haessler et al 4,130,881; Yasaka et al 3,970,996; Zonneveld et al 3,829,844; McCormick et al 3,794,982; and Worthington et al 3,566,370.

However, these systems do not provide a simple, yet reliable, interactive method of presenting data from a data base to a knowledgeable operator with the flexibility of revisions and modifications. Generally, the difficulties of the systems lie in the arrangement of the data base, the classification of the information in the data bases, and the ability to progress through the data base.

SUMMARY OF THE INVENTION

The method and system of the present invention utilize a general purpose, programmable and programmed digital microcomputer to make a diagnosis of a condition based on the responses to a series of choice menus sequentially presented to the operator. While the presently preferred embodiment of the present invention is used for providing a diagnosis in dermatopathology, the present invention can be utilized in any particular area in which there are a plurality of conditions which can be grouped into a plurality of levels with each level having a greater degree of specificity or particularity. Each level is comprised of a number of sets and the entire level covers the universe of the subject.

In a particular embodiment of the present invention, an operator is presented with a set containing a number of changes to select. When the operator indicates the selection in a particular set, the selection is tied through an accompanying pointer or indicator to a succeeding set of changes to select located in a lower or further level. Finally, the classification is performed when the last selection in a chain is reached, which selection is identified by a particular identificaton means.

The present invention provides both a tool for classification of an item and an instructional aid for use in training and education. The present invention finds particular application in those areas that are amenable to a systemic approach. One such area as mentioned above is dermatopathology. As used herein, diagnosis means the determination of the condition of a biopsy based on an evaluation of a set of observed conditions and findings. A differential diagnosis refers to the presentation of a number of possible diagnoses which could possibly result from the selected conditions.

Thus, the present invention is directed to the retrieval of information stored in a data base that can be conceptualized as being arranged in an ordered set of levels or columns. In a preferred embodiment of the present invention, the data in each level is linked in both directions to a previous level and to a subsequent level. Thus, the data base is arranged in a particular hierarchy.

The present invention can be conceptualized as both an interactive, automated method utilizing a computer system for performing a differential diagnosis based on characteristics or changes in the condition of a patient, including a biopsy or other specimen or test result, and as an interactive computerized system for performing a differential diagnosis based on characteristics or changes.

A method according to the present invention utilizes a computer system having a memory means for storing an array of sets of changes and diagnoses, an output means for presenting a plurality of selected changes or diagnoses to an operator, an input means for entering operator selected responses, and a processor means for receiving the selected responses, for retrieving a set of changes or diagnoses stored in the memory means, and for providing the retrieved set to the output means. The method comprises the steps of presenting a first set of medical changes on said output means, each change having a linkage or a pointer to a further, unique set of changes; selecting a change from the presented first set and entering the selected change with the input means; and retrieving from the memory means a set of further changes identified by the linkage associated with the selected change, each further change having a linkage to a still further unique set of changes. The identified set of further changes is then presented on the output means and one of the presented changes is selected and entered with the input means. The retrieving, presenting, selecting and entering steps are repeated until an identifiable final selection is obtained, the final selection including means for identifying it as being a final selection.

In a particular embodiment of the present invention directed to the field of dermathopathology, the particular embodiment includes an interactive computerized system for performing a differential diagnosis of a biopsy based on the characteristics or changes of the biopsy product. The system comprises an output means for presenting a set of a plurality of selected histopathological changes to an operator, an input means for entering operator selected responses, a memory means, and a processor means under program control. The memory means is for storing a hierarchical data base and the processor means is for responding to the operator selected responses for retrieving further data stored in the memory means to the output means. The data base is comprised of a plurality of downwardly linked files, each file comprised of a header record and a plurality of data records where the operator selected response corresponds to one of the data records. The header record is comprised of a file identification field and each of the data records is comprised of a linking identifier field and a data field. The data field contains a histopathological change when the identifier field contains an entry of a file identifier that points to a data record located below in the hierarchy, and the data field contains a differential diagnosis when the identifier field does not contain such a file identifier. Other objects, advantages and aspects of the present invention are set forth in or are apparent from the detailed description of the presently preferred embodiment set forth hereinbelow.

BRIEF DESCRIPTION OF THE DRAWINGS

FIGS. 7a through 7e are reproductions of data displayed on a terminal according to the present invention in which one diagnosis in dermal pathology is made.

FIGS. 8a through 8e depict the various data files as stored in the data base according to the present invention and from which the corresponding components of FIG. 4 are generated by the computer program.

DESCRIPTION OF THE PREFERRED EMBODIMENT

Figure 1:
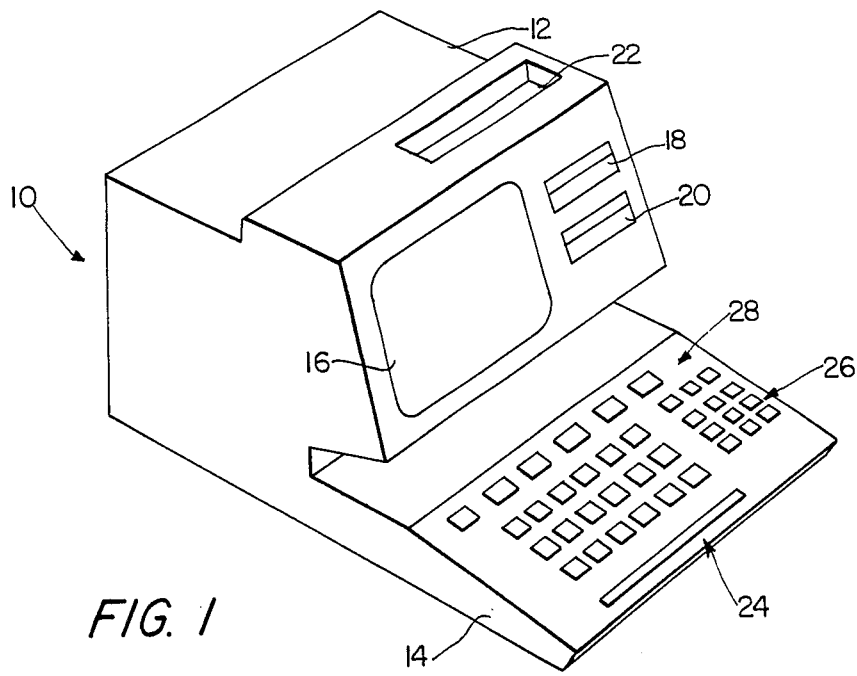
FIG. 1 is a perspective view of a microcomputer useable in performing the method of the present invention.

With reference now to the figures wherein like numerals represent like elements throughout the several views, and in particular with reference to FIG. 1, a general purpose, programmed microcomputer 10 is depicted. Microcomputer 10 is housed in a cabinet 12 and includes a keyboard 14 for entering data into the computer, a CRT 16 for displaying output data, and two floppy disks drives 18 and 20. A printer, not shown, is also mounted inside cabinet 12 and produces a hard copy output on paper that exits through a slot 22 located at the top of cabinet 12. Keyboard 14 is generally divided into three sections, an alphabetic section 24, a numeric key pad 26, and a plurality of function keys, generally shown at 28.

The electronics of microcomputer 10 are conventional and include a microprocessor, interface circuitry, internal ROM memory and RAM memory, and an electrical power supply (all not shown).

The present invention, however, is directed to a data base stored in the computer memory or on floppy diskettes and the sequential, ordered presentation of that data to an operator by microcomputer 10 programmed with a computer program. Depending upon size, the data base is usually stored on two or more floppy diskettes mounted on disk drives 18 and 20. However, for very large data bases, other disk drives can be connected to microcomputer 10 as needed. An operating system program can be stored on the ROM memory, and the applications computer program for creating the data base and/or for retrieving and presenting the data can also be stored on ROM, or on a floppy diskette.

The data base is comprised of a plurality of questions or statements about a characteristic of an item, such as a biopsy of a human patient's skin. Related questions are grouped into a set, which normally has from two to nine questions. Related sets are figuratively grouped into a column or level, and the data base is comprised of a plurality of levels. The data base also is comprised of other data which provides information about a set or is used as a pointer to link one set to another.

In a specific embodiment of a data base according to the present invention, listed in Table I, the area of dermatopathology is covered. Each question in the data base is directed to a diagnostic change in a dermatopathological biopsy. Each set of questions presents a group of related changes, one of which is to be selected by the operator. Each level in the data base of the present invention essentially covers the entire universe or realm of possible changes at a particular state of specificity. An an initial specific example, which is described in greater detail below, the initial or first level presents three choices to the operator; epidermal, dermal or subcutaneous and the operator selects one of them. Thus these three choices cover the entire realm of changes in a dermatopathological biopsy.

The data base according to the present invention is arranged in the form of a decision tree. The data base is comprised of a plurality of relatively located data files that normally are accessed in a predetermined sequence, or alternatively can be randomly accessed. The data files, in turn, are comprised of a plurality of fixed length data records, and each data record is comprised of two fixed length fields.

Figure 2:
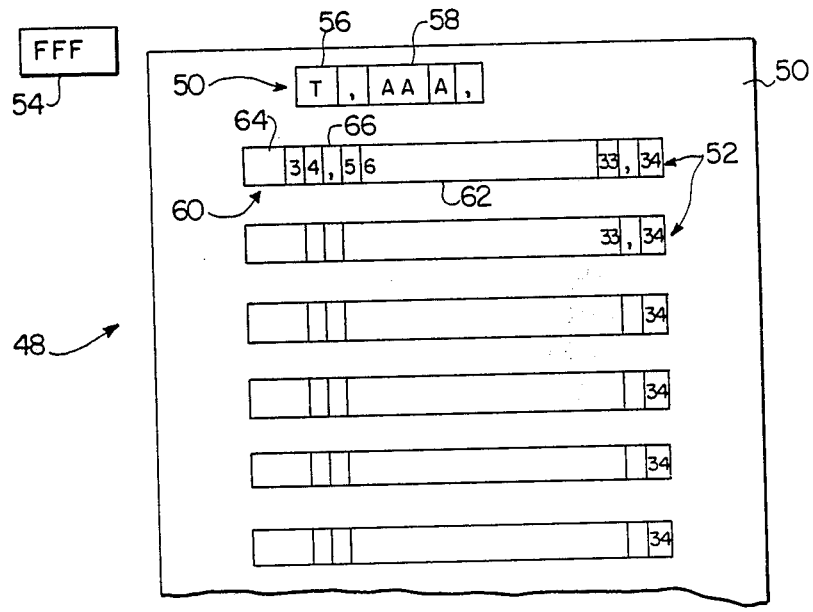
FIG. 2 is a diagrammatic representation of a data file depicting the data records and fields.

A data file is diagrammatically depicted at 48 in FIG. 2. The file is comprised of a first program or header record 50 followed sequentially by up to nine data records 52 (only seven data records being depicted). Each data file 48 is identified by "name", which in the present embodiment consists of a decimal number diagrammatically indicated in a box at 54 and represented by "FFF". As is well known, the names of data files are stored by a compiler computer program in a look-up table and are keyed there to the address of the data field in the data base. Thus a file name does not appear in the data file itself.

Header record 50 contains two fields, a TOTAL field 56 and an antecedent field 58. TOTAL field 56 is a one or two character wide field that contains the number of data records 52 contained in the particular file. Antecedent field 58 is three characters wide and contains the backward or upward file pointer or linkage to the file that called the present file. All files except the first file or initial file in the data base have an antecedent pointer, which is the numerical name of the field.

Each data record 52 is comprised of two fields separated by a comma, a first field 60 and a second field 62. First field 60 extends from character number one through character number four, and second field 62 begins at character position six and extends through character position thirty-four. Thus, first data field 60 is four characters long and second data field 62 is twenty-eight characters long. First data field 60 contains a three character long subfield 64 which contains a pointer or subsequent file linkage and a one character long diagnostic indicator subfield 66. Normally, file linkage subfield 64 contains the file identification of the next immediate lower file in the hierarchical data base. However, when the particular file contains diagnostic information and thus is the bottom file in the particular linkage chain, subfield 64 is empty. This condition is used by the computer program to ascertain that the particular file is a diagnostic file. In most cases, diagnosis indicator subfield 66 is empty. However, in the next to the last file in the linkage chain, subfield 66 may contain the identity of the data record in the last file in the linkage chain which contains the probable diagnosis. As discussed below, the computer program detects the presence of an entry in subfield 66 and causes the linked data field to flash on CRT 16.

Figure 3:
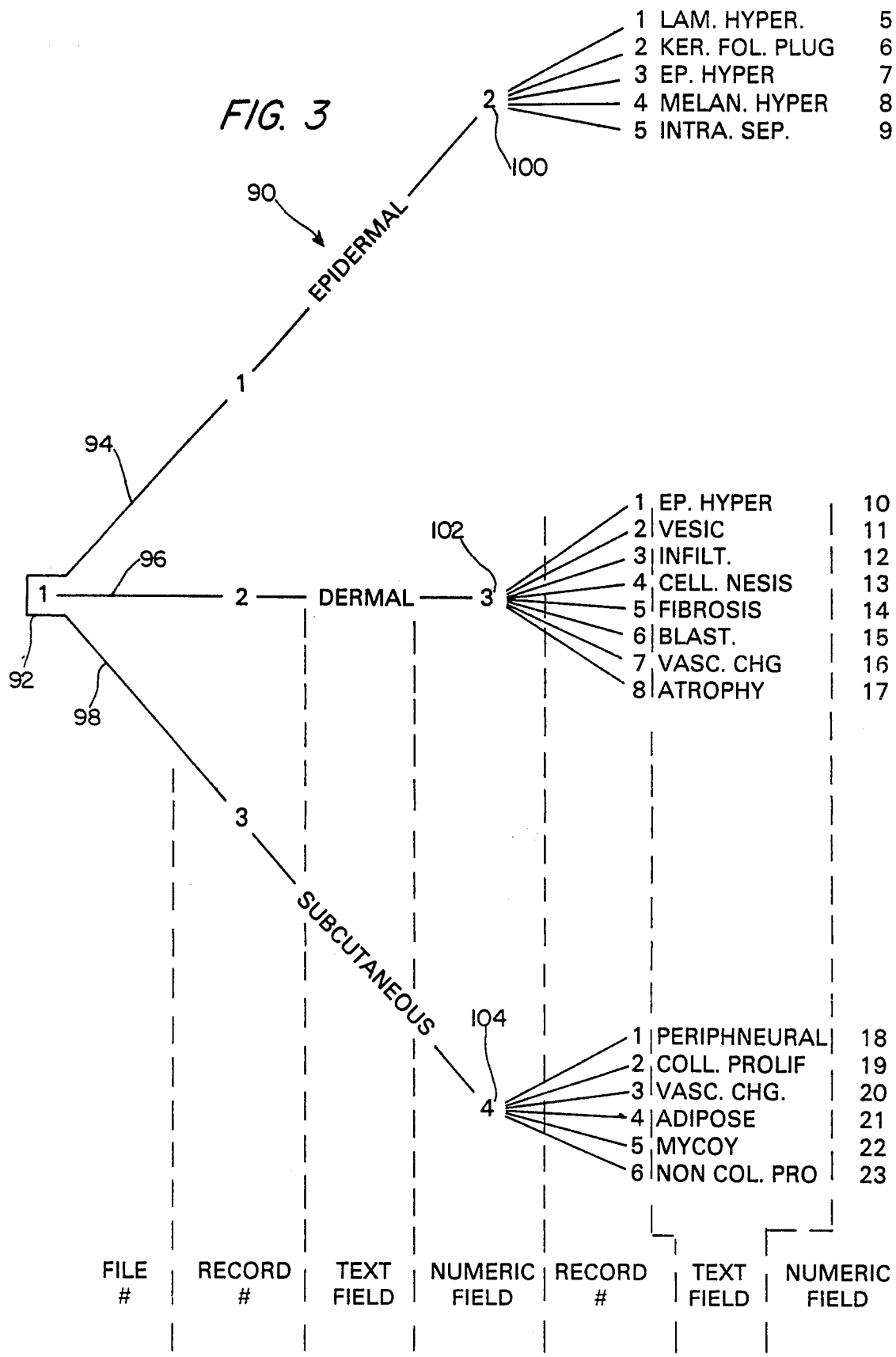
FIG. 3 is a schematic diagram of part of a decision tree hierarchical arrangement of data in a data base.

The hierarchical data base is schematically represented through three levels or columns in FIG. 3 for a presently preferred embodiment of the present invention directed to dermatopathological diagnosis. As can be clearly seen from FIG. 3, the data base is arranged in the form of a decision tree 90. Tree 90 has a trunk 92 that encompasses all histopathological changes known to involve any layer of the skin. Trunk 92 is divided into three branches, a first branch 94, a second branch 96, and a third branch 98. As the tree develops with progressively smaller branches being connected to the three major branches, more and more branches are located in a given level or column. Each column comprises an entire set of possible changes or possibilities at a predetermined degree of specificity. Each branch gives rise to further branches through an indicated node that represents a new file. The branches from the node correspond to the records in that file. Thus, it can be seen that each record is linked to a subsequent file which corresponds to the next node of the decision tree. Consequently, the subsequent files progressively divide and subdivide the data contained in the data base. Furthermore, the total number of changes increases from a higher level or more general column to a lower level or more specific column until diagnoses are reached. Once a diagnosis is reached, the chain is terminated at that column.

In FIG. 3, branch 94 represents changes occurring in the epidermal part of the skin, branch 96 represents the changes occurring in the dermal part of the skin, and branch 98 represents changes occurring in the subcutaneous layer of the skin. Epidermal branch 94 terminates in node 100, dermal branch 96 terminates in node 102 and subcutaneous branch 98 terminates in node 104. Nodes 100, 102 and 104 each contain from five to eight branches, and each branch is further subdivided (not shown in FIG. 3) into yet further branches at particular nodes.

At the bottom of FIG. 3, the particular data or numbers located on the various branches are labelled by the corresponding part of the data base. Thus, trunk 92 corresponds to file number one, record numbers one, two, and three correspond to data records 52 of FIG. 2. Each data record, in turn, is comprised of a text field and a numeric field, the numeric field appearing at nodes 100, 102 and 104. The record number with a text field appearing on a branch and terminating in a numeric field appearing at a node is replicated from each of nodes 100, 102 and 104. The hierarchical data base continues until all of the possibilities are exhausted. FIG. 8 contains selected portions of the data base, and reference may be made to Table Ia to see more of the data base, and will be referred to for specific examples hereinbelow.

Figure 4:
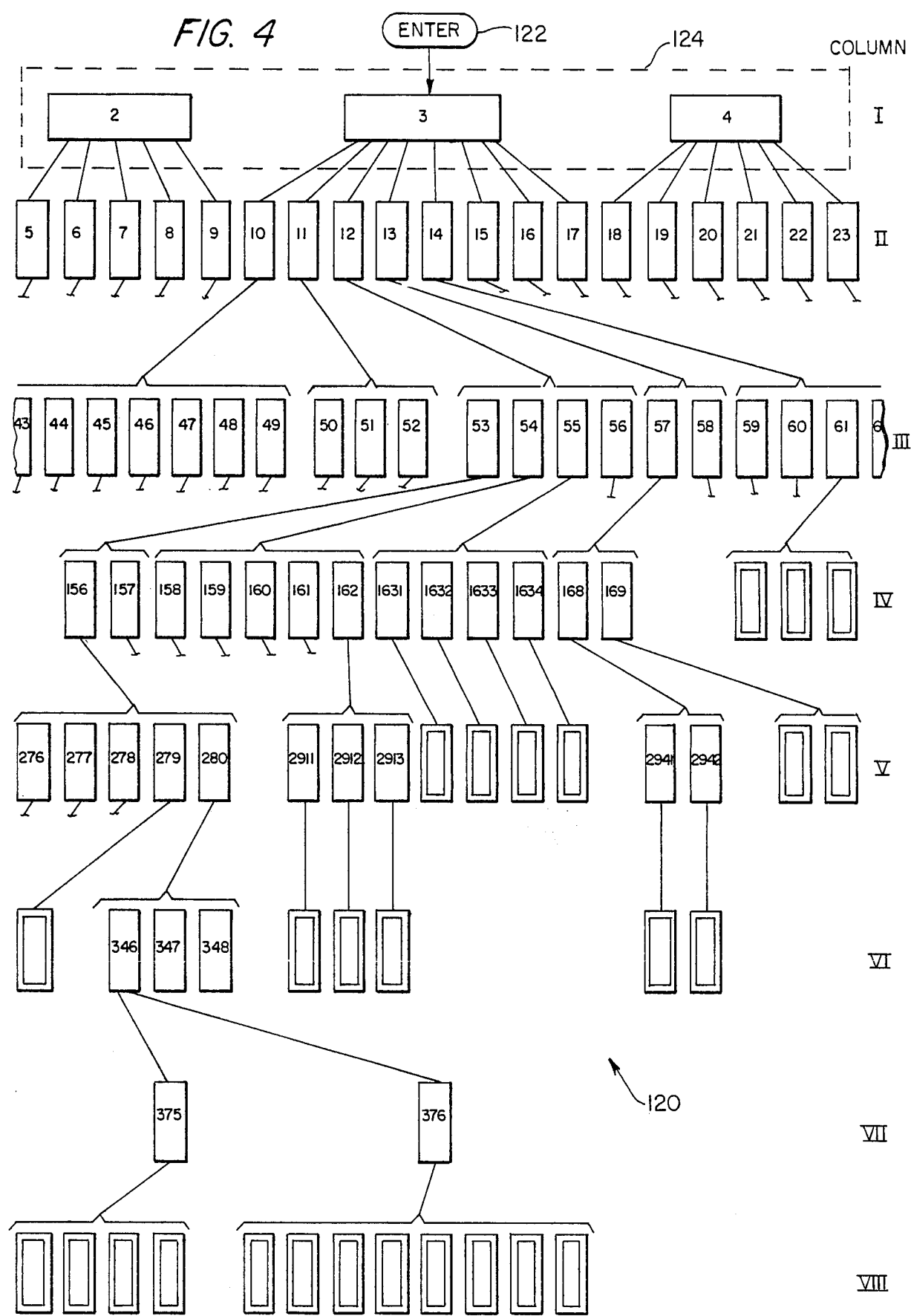
FIG. 4 is a schematic block diagram of part of the decision tree, depicted in a different form than that depicted in FIG. 1, and showing the data base arranged in eight levels.

With reference now to FIG. 4, a diagrammatic representation of a data base 120 is depicted. Data base 120 is a hierarchical data base that is linked in a decision tree configuration, and represents the actual data base for the area of dermatopathology. An entire data base 120 is depicted, in Table Ia, while part of the actual data base arranged in a file and record presentation is depicted in FIGS. 8a through 8e. The numbers in the boxes in FIG. 4 correspond to the file "names" or numbers depicted in FIGS. 8a through 8e, and stored in a file name table (not shown). However, because of the problems of space, FIG. 4 does not encompass all of the files depicted in Table Ia.

Data base 120 is entered through an entry point diagrammatically shown at 122. Progression through data base 120 proceeds from entry point 122 to an initial or first file 124, which also comprises column I of data base 120. Data base 120 can be conceptually thought of as being arranged into eight levels or columns of files. Each file is numbered and the corresponding number with the appropriate entries can be found in FIGS. 8a through 8e. Each file containing a change or characteristic is indicated by a single rectangular box and each file containing a decision is indicated by a double rectangular box. For example, from entry point 122, selections could be made such that the progression through the data base would go through initial file 124 where data base file 3 was selected, then data base file 14 was selected, and then a selection had to be made from data base files 59, 60, 61, or 62. If data base file 59 were selected, progression would proceed. However, if data base file 61 were selected, then progression would terminate in column 4 of the data base upon the presentation of three choices for a diagnosis. In data base 120, the first file of diagnoses is not reached until column 4. Thus, data base 120 proceeds exponentially to level or column 4 where the rate of increase of further choices begins to decrease. Consequently, the largest data base column is column 5, which contains a number of diagnoses files, which as mentioned above, terminate the progression through the data base. Columns 6, 7, and 8 are thus progressively smaller. In effect, data base 120 can be conceptualized as having either a rough diamond configuration or a rough bell-shaped curve, depending upon how the columns are stacked.

DATA BASE CREATION

Figure 5:
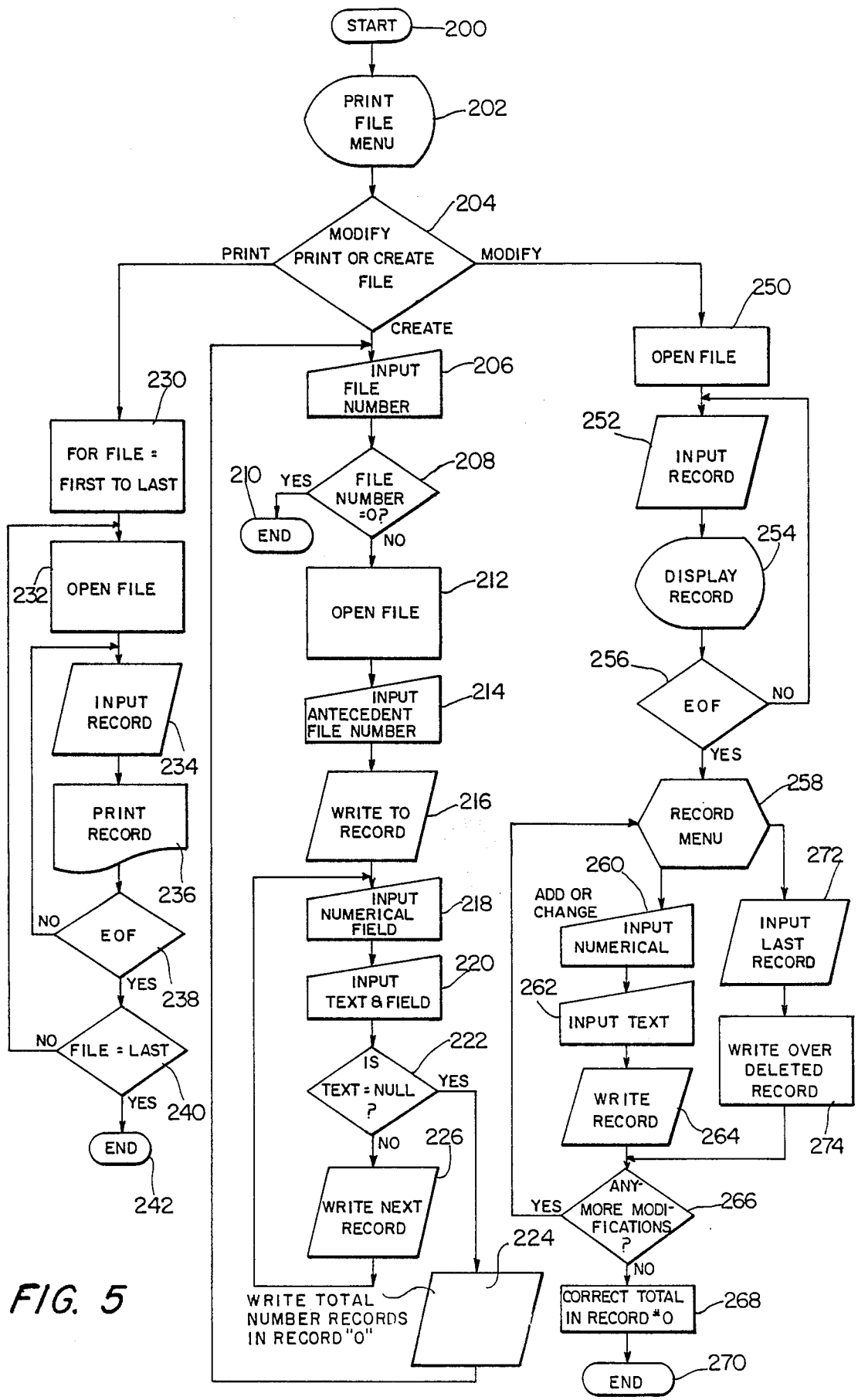
FIG. 5 is a schematic flowchart of a computer program for creating the data base shown in FIGS. 3 and 4.

With reference now to FIG. 5, a computer program is depicted in a schematic flowchart for creating data base 120, a current embodiment of which is depicted in Table Ia as an edited alphnumeric dump from memory. Table Ib is a sequential dump of the first file in hexadecimal with alphanumeric equivalents. Data base 120 is also shown diagrammatically in FIG. 4. A computer program for creating data base 120 is depicted in Table II. This computer program is written in TI Extended BASIC, a programming language for the Texas Instrument home computer Model 99/4 that is described in Texas Instruments Incorporated publications.

The decision tree filling computer program begins in a start terminal 200 and proceeds to display box 202 whereby the computer displays a file menu. An abbreviated file menu is depicted in line 220 in Table II. The operator makes a selection from the file menu which is shown in FIG. 5 by decision diamond 204. The corresponding parts in Table II are line 230 and 240.

Assuming the operator selects the "create" choice, the program proceeds to input box 206, which also corresponds in Table II to lines 250 and 260. The program checks whether an error has been made and if the file number is read as a "0", then the program branches in decision box 208 to terminal 210 where the program terminates. Alternatively, and as depicted in Table II, the program can simply branch back to display box 202.

A further choice would be to have the program display an error menu.

Assuming that the file number is correct, the program proceeds to process box 212 where a new file is opened. The opening of the new file is indicated in Table II at lines 270 through 330. The new file is essentially opened by the program proceeding from process box 212 through an input box 214 where the antecedent file number is received and written to the record by I/O box 216. The antecedent file number is the number of the preceding file in the decision tree. For example, with reference to FIG. 4 and Table Ia, the antecedent of file 61 is the number 14, which represents the file name of file 14. The antecedent of file 14, in turn, is the number 3, which is the name of file 3.

From I/O box 216, the program proceeds in a loop whereby the numerical field is received by input box 218 and the text field is received by input box 220. The numerical field represents the pointer or linkage to the next proceeding file should that selection that appears in text field 220 be selected by the operator.

From input box 220, the program proceeds to decision box 222 where it asks if the variable "TEXT$" is a null field. The variable TEXT$ is defined in the program depicted in Table II at line 400 and represents the alphanumeric entry having a maximum length of 28 characters and representing the characteristic to be displayed on the screen. For example, with reference to FIG. 4, in file 14 (in column II), the numerical field would be the numbers 59, 60, 61, or 62 and the text fields would be, for example for the number 62, the following words "Nonsclerosing Nonpolypoid". While the text field can have any length, by the program depicted in Table II at line 400, the maximum size is set at 28 characters. This selection is chosen as a compromise between the maximum amount of data desired on the one hand, and the realistic size of the data storage medium. If a hard disk is used, instead of floppy disks, for storage of the data base, then obviously the file sizes can be much larger, thereby permitting the record size which contains the variable "TEXT$" to be larger.

In decision box 222, the program checks whether the variable "TEXT$" is a null, that is, there is no entry. As seen in Table II at lines 400 and 450, if the operator has not made an entry the program branches to I/O box 224 where the number of records in the file is written in record number 0. Then, the program branches back to the input box 206 to resume the loop. On the other hand, if the variable "TEXT$" has a value, then the program branches to I/O box 226 where the next record is written and then the program loops back to input box 218 where an additional record is received.

The operation of decision box 222 in the program can be seen with reference to file 14 in column II of FIG. 4. As a result of entries made to fill file 14, the program would branch at decision diamond 222 a total of four times through I/O box 226 to the top of input box 218 and then would branch to I/O box 224 to accept a new file number at input box 206.

The program in the file create mode continues looping until the file number is printed as a "0" and the program ends at terminal 210.

The decision tree filing program depicted in FIG. 5 also permits, by operator selection at decision diamond 204, either modification of an existing file or the printing of a file. If the print mode is selected, the program branches from decision diamond 204 to a process box 230 where a "FOR NEXT" operation is performed to print from the first file to the last file. The "FOR NEXT" loop comprises a process box 232 in which the program opens a file, an I/O box 234 where an input record is retrieved from memory and stored in the active computer memory, and a print box 236 whereby a hard copy of the record is printed. The program then proceeds to a decision diamond 238 where the program checks whether it is the end of the file. If the file contains more records, the program branches back to the top of I/O box 234. The program continues to loop until the last file in the record is received and then the program branches to decision diamond 240. In decision diamond 240, the program ascertains whether the completed file was the last file as indicated in the "FOR NEXT" loop. If the last file has been printed, then the program proceeds to terminal 242 where the program ends. On the other hand, if the file is not the last one, then the program branches from decision diamond 240 back to the top of processing box 232 where a new file is opened.

An existing file can be modified by the procedures depicted in the branch from decision diamond 204 to a processing box 250. In processing box 250, the program opens an existing, indicated file and proceeds to I/O box 252 where the program retrieves a record from a file stored in memory. The program then proceeds to display box 254 where the retrieved menu is displayed on the terminal. From display box 254, the program proceeds to a decision diamond 256 where the program asks if the record is the last record in the open file. If it is not, the program branches back to the top of I/O box 252 where another record is retrieved from memory. The program proceeds in the loop until all of the records of the open file have been displayed. Then, the program branches to a subroutine in pre-defined process box 258. In pre-defined process box 218, the program executes a subroutine to display a choice on the terminal for the operator to select. If the operator selects an "add or change", the program proceeds to input box 260 where the program receives a numerical input. From input box 260, the program proceeds through a further input box 262 where the text is received and then to I/O box 264 where the new record is written. Form I/O box 264, the program proceeds to a decision diamond 266 in which the program asks if there are any more modifications. If there are no further modifications, the program branches to process box 268 where the "total" field in the header record of the opened file is corrected to reflect the addition or changed record. From process box 268, the program proceeds to terminal 270 where the program ends.

If the operator selects an option indicating that the last record has been corrected, the program proceeds from pre-defined process box 258 to an I/O box 272 where the last record is retrieved from memory. Form I/O box 272, the program proceeds to processing box 274 where the record is written over the deleted record in memory and the program then proceeds to the top of decision diamond 266, where the program again asks if there are any further modifications.

DIFFERENTIAL DIAGNOSIS GENERATION

Figure 6:
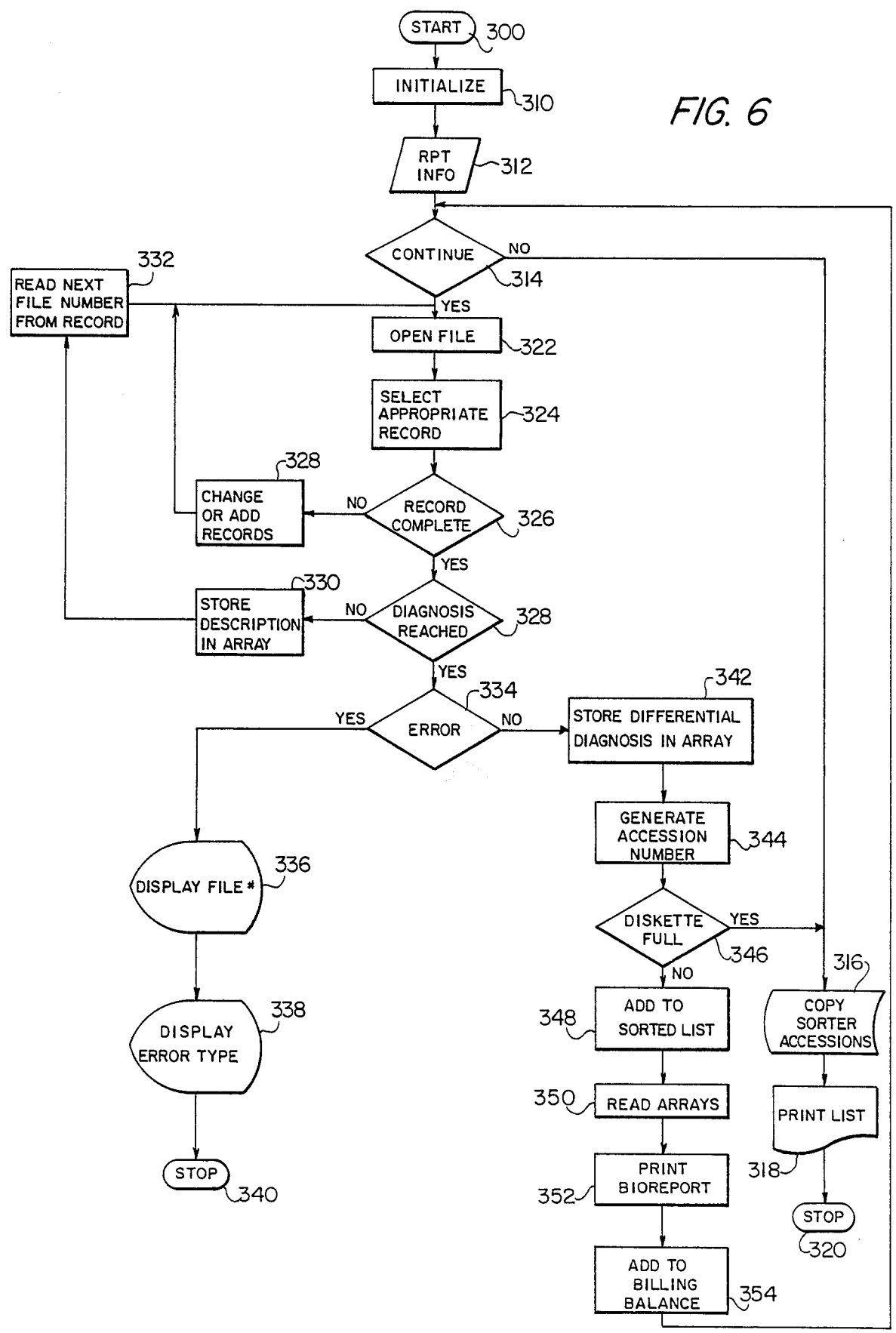
FIG. 6 is a schematic flowchart of a computer program according to one embodiment of the present invention.

With reference now to FIG. 6, a flowchart of a computer program for generating a differential diagnosis and printing a biopsy report utilizing a data base according to the present invention is depicted. Part of the actual computer program, again written in TI extended BASIC is depicted in Table III.

The program begins at start terminal 300 and proceeds to a process box 310 in which the program initializes a number of variables used in the program and also dimensions a number of arrays and strings. Process box 310 is essentially representative of lines 190 and 260 of the program in Table III. From process box 310, the program proceeds to an I/O box 312 in which the program receives information for printing a report through interaction with an operator. A sample of an actual report generated by an embodiment of the present invention and the program depicted in Table III is shown in Table IV. I/O box 312 corresponds to lines 210 through 240 in Table III. From I/O box 312, the program proceeds to a decision diamond 314 in which the program determines whether the operator wishes to continue or to terminate the particular program. If the operator selects to terminate the program, the program branches to on-line storage box 316 in which the sorted accessions are copied, then to print box 318 which makes a hard copy print out of the activity, and finally to stop terminal 320, at which point the program terminates.

If the program determines at decision diamond 314 that the operator desires to continue, the program proceeds to process box 322 where a file is opened. Process box 322 roughly corresponds to lines 280 through 340 in Table III. From process box 322, the program proceeds to process box 324 in which the program determines the operator selected record and retrieves it from memory. From process box 324, the program proceeds to a decision diamond 326 in which the program determines whether the operator has indicated that the record is complete. This roughly corresponds to lines 420 and 430 in Table III (but the actual modification subroutine is not included in Table III). If the record is not complete, the program branches to process box 328 in which modifications can be made to the record and then the program returns to the top of process box 322. The ability to modify a record, while provided for in this computer program depicted in FIG. 5, is also provided for in this program of FIG. 6 for the convenience of the operator. The modification of the record proceeds quite similarly to that described above with respect to FIG. 5.

If the record is complete and no modification is desired, the program proceeds from decision diamond 326 to decision diamond 328. Decision diamond 328 corresponds to line 425 in the computer program depicted in Table III. Essentially, the program determines whether a diagnosis has been reached by asking whether there is an entry in the first data field 60 of a data record 52 as depicted in FIG. 2. Stated another way, the program is asking whether, for example, there is a number preceding the text in file 12 (see FIG. 8c). In the case of file 12, all four records have a numeric entry in the field. Therefore, the result of any selection made from the choices supplied by file 12 and as ascertained by decision diamond 328 in FIG. 6 would be negative and the program would branch to process box 330. In process box 330, the program stores the selected text description in an array, called "D$(D)" in the computer program depicted in Table III. Line 470 of the computer program in Table III corresponds to process box 330. From process box 330, the program proceeds to process box 332 where the program reads the number of the next file from the chosen data record. In essence, the program identifies a variable by the number located in first data field 60 of the chosen data record 52 (see FIG. 2). Line 480 in Table III is essentially the equivalent of process box 332. From process box 332, the program loops back to the beginning of process box 332 where the identified file is opened.

If the program determines that there is a null field in first data field 60, then the program branches from decision diamond 328 to a further decision diamond 334. An example of a null field is shown in FIG. 8e in file 163.

An alternative method of determining when a diagnosis has been reached is to assign a particular series of numbers to all of the fields containing diagnoses. For example, all such fields could have a file number greater than 800. Yet another method of determining whether the identified file contains only diagnoses is to insert a code into the data field. Such a code could be a letter or a unique number. Still other methods or procedures for determining when a diagnosis is reached would be obvious to those skilled in the art.

From decision diamond 334, the program determines whether there is an error and if there is, the program proceeds to display box 336. Decision diamond 334 corresponds to line 330 in the computer program depicted in Table III and display box 336 corresponds to line 2020 in Table III. In display box 336, the number of the file containing the error is displayed and the program proceeds to display box 338 where the type of error is displayed. Then the program proceeds to stop terminal 340 in which the program terminates pending correction of the error.

If no error is detected in decision box 334, the program branches to process box 342 in which the differential diagnosis is stored in an array and the program proceeds to decision box 344 where an accession number is generated. The accession number generated in process box 344 is a number assigned to the particular biopsy case and in the present embodiment is simply the next numerical number in the sequence of biopsies previously performed. Alternatively, other report numbers could be generated which would have an accounting or medical meaning.

From process box 344, the program proceeds to decision diamond 346 where the program determines whether the particular storge diskette is full. Obviously, this program is designed to run on a system using floppy diskettes as a storage medium to contain the generated reports. If the diskette is full, the program branches to storage box 316. If the diskette is not full, the program branches to process box 348 and the heading of the present report is added to a data base containing sorted lists of previous lists. From process box 348, the program proceeds to process boxes 350, 352, and 354 where the program reads the arrays, prints the report, and runs a financial subroutine to take care of the appropriate billing. From process box 354, the program branches back to the beginning at decision diamond 314 where the operator is asked whether the program should be continued.

DISPLAYS

Reference is now made to FIGS. 7 and 8 in which a differential diagnosis of a biopsy has been made. FIGS. 7a through 7e depict the display appearing on the terminal and from which the operator makes the appropriate selections. The selection made by the operator is depicted under the word "choice". FIGS 8a through 8e depict corresponding boxes showing the information as it is depicted in the data base, with the exception as noted above that the "file number" does not actually appear in the data base. As mentioned above, the file number is really the name of the file and indicates the address at which the data is stored. Not shown in FIG. 8 but shown Table Ib at the top is the TOTAL field 58 which indicates to the computer the total number of data records contained in that file (which is 3).

FIGS. 7 and 8 can also be used to describe the operation of the present invention. When the program depicted in FIG. 6 is loaded, the first screen to be presented to the operator by process box 322 in FIG. 6 is that shown in FIG. 7a. In essence, the operator is asked to select a number from 0 through 4 with the record at number "0" representing a selection of the antecedent file number and the number "4" is a call to a modification subroutine represented by decision diamond 326 and process box 328 of FIG. 6.

As a result of observations from the biopsy and as a result of the detected changes, the operator has decided that the changes occur in the dermal layer of the biopsy and thus has selected the number 2 and pressed that number on keyboard 14 (FIG. 1). As shown in FIG. 8a, the selection of choice "2" is translated by the computer to file number "3" and the program closes file 1, the initially presented file, and proceeds to open up file 3 which is depicted in FIG. 8b. This translation step is essentially an aid to the operator so as to avoid confusion. It can be seen that it is easier for an operator to always select a number from 0 through 9 rather than the particular file number. On the other hand, the file numbers are used by the computer to open the designated file by retrieving it from memory.

Returning to FIG. 7, and in particular FIG. 7b, the next display which is shown to the operator is depicted. As mentioned above, this display results from the selection of choice 2 from the menu presented in FIG. 7a. As shown in FIG. 4, the operator is proceeding through the data base from column I with the selection of the appropriate record to column II. The operator then selects the choice presented in FIG. 7b by pressing the appropriate number on keyboard 14. In the particular example, the operator chose the number 3, which by reference to FIG. 8b, represents the selection of file 12. The program then proceeds to column 3 in FIG. 4 and the data depicted in FIG. 7c is next presented to the operator.

By observing the biopsy, the operator has selected choice 3 and made that input on keyboard 14. Selection 3 in FIG. 7c corresponds to file 55 in FIG. 8c.

Not shown by the parts of FIG. 7, the operator has determined that the file depicted in FIG. 8c should be modified and has accordinly modified it as indicated in FIG. 7c. The added selections 5 through 8 would be given unique file numbers. As mentioned above, the operator makes the modification be selecting choice 9.

In the present example, as mentioned above, the operator has chosen selection 3 which corresponds to a request to the computer to retrieve file number 55. The data in file 55 is depicted on a screen to the operator and is shown in FIG. 7d. In the present example, the operator has next selected choice number 1 which corresponds to the first data record. Referring to FIG. 8d, it can be seen that for the first time the number in the numeric field is a four digit number. This four digit number is broken up by the computer into a first file linkage or pointer subfield, such as subfield 64 in FIG. 2, and a diagnosis indicator subfield of a single digit, such as subfield 66 in FIG. 2. The codes in the subfields of the selected penultimate file are used by the program to indicate the most appropriate diagnosis. The number of the selected diagnosis in the ultimate file is flashed on the screen as a result of processing lines 580 and 590 of the program depicted in Table III. The corresponding display is shown in FIG. 7e. It is also noted that file 163 is determined to contain diagnoses by the absence of a number in the numeric field, as shown in FIG. 8e.

The present invention has now been described with respect to a presently preferred embodiment thereof. Obviously, the data base will vary with respect to the particular field being investigated. However, so long as a computer program such as that depicted in FIG. 5 is used to create the data base, the computer program as depicted in FIG. 6 can be used to make the sequential choices and achieve a suggested diagnosis. In the aforedescribed example, the program proceeded only through level 5. However, as shown in FIG. 4, a different set of files could be selected such that all 8 levels would be traversed. This can be seen by referring to FIG. 4 and comparing it with the data in Table I for the following example of selected records: 3, 12, 53, 156, 280, 346, and 376.

Other changes and modifications to the present invention would be obvious to those of ordinary skill in the art.

TABLE Ia

```
DERMATOPATHOLOGY DATA BASE

COPYRIGHT (C) 1984 BRIAN POTTER MD

PAGE    1

2EPIDERMAL3DERMAL4SUBCUTANEOUS5LAMINATED HYPERKERATOSIS6
FIBROUS FOLLICULAR PLUGGING7EPITHELIAL PROLIFERATION8MELANOCYTIC PROLIFERATION9
INTRAEPIDERMAL SEPARATION71DEGENERATED EPIDERMIS40PARAKERATOSIS SPARSE INFLTRN1
EPITHELIAL PROLIFERATION11VESICULATION12INFILTRATION118PHAGOCYTOSIS OF PIGMENT1
COLLAGENOUS PROLIFERATION15ELASTOSIS16VASCULAR CHANGES17ATROPHY19
COLLAGENOUS PROLIFERATION20VASCULAR CHANGES21ADIPOSE TISSUE CHANGES22MYOCYTIC23
NONCOLLAGENOUS PROLIFERATION28OGRANULOMATOUS INFLAMMATION24DERMAL PAPILLOMATOSI
25NO PAPILLOMATOSIS26PARAKERATOTIC PERFORATION27INFUNDIBULAR HYPERKERATOSIS28
PAPILLATED EPIDERMIS29ATYPICAL PALE CELLS30WITH DERMAL PAPILLOMATOSIS31
SUBEPIDERMAL BASALOID CELLS32DERMAL VASCULAR INFLAMMATION33DYSKERATOTIC CELLS34
LOBULES OF HYALINIZED CELLS35EXOENDOPHYTIC NEOPLASM36INDIVIDUALLY37
NESTS AND NORMAL CELLS38ATYPICAL CELLS AND NESTS39VESICULAR42ACANTHOLYTIC41
PUSTULAR43CYSTIC44FOLLICULAR45ENLARGED SEBACEOUS LOBULES46
```

SMALL DUCTAL DIFFERENTIATION47BASALOID HORN CYST NEOPLASM48
NEOPLASTIC IN FIBROUS STROMA49SOLID MASSES WITH FEW LUMENS258
DARK-STAINED & SHADOW CELLS50SUBEPIDERMAL WITH INFILTRATN51
SUBEPIDERMAL WITHOUT INFLN52INTRADERMAL53LEUCOCYTIC23CELLULAR NONCOLLAGENOUS55
EXTRACELLULAR ACCUMULATION56INCREASED AMOUNTS OF MUCIN13PIGMENTED CELLS355
CELLS WITH FOAMY CYTOPLASM13CELLULAR NESTS358CELLULAR AND COLLAGENOUS280
GRANULOMATOUS57MONOMORPHOUS NEVUS CELLS58MELANOCYTES118PHAGOCYTES59
PERIFOLLICULAR60PAPILLOMATOUS61HOMOGENEOUS SCLEROSIS62NODULAR FIBROMATOUS60
FIBROBLASTS & TELANGIECTASIA275INFLAMMATORY AND FIBROTIC63PERFORATING64
IN THE PAPILLARY CORIUM65IN THE RETICULAR CORIUM66INFLAMMATION67THROMBOSIS68
DILATED VESSELS69HYPERPLASTIC PROLIFERATION70ABERRANT NEOPLASTIC CHANNELS84
CELLULAR NEOPLASIA71SCLEROSING72NONSCLEROSING76NONAGGRESSIVE UNENCAPSULATED77
FIBROUS HYPERCELLULAR74NEURAL CELL NEOPLASIA66SMALL VESSEL INFLAMMATION67
SMALL VESSEL THROMBOSIS81ARTERIAL INFLAMMATION82VENOUS THROMBOSIS83
NONNEOPLASTIC HYPERPLASIA84CELLULAR NEOPLASIA85LYMPHATIC NEOPLASIA207
SEPTAL VASCULITIS IN THE FAT209VASCULITIS IN FATTY LOBULES86
INFLAMMATION WITHIN SEPTA87INFLAMMATION WITHIN LOBULES88ATROPHY89NONNEOPLASTICS
GLOBOID MATURE ADIPOCYTIC91POORLY DIFFERENTIATED TUMOR92
INTERLACING SMOOTH MUSCLE93STRIATED CELL PROLIFERATION75
INFILTRATIVE SPINDLE CELLED73ENCAPSULATED NEURAL TISSUE54MONOPHASIC PALE CELLS
199MYXOID HISTIOCYTIC78FIBROUS DIFFERENTIATION200MULTINUCLEATED GIANT CELLS355
CELLS WITH FOAMY CYTOPLASM117PLASMA CELLS100EPIDERMIS THIN101
HYPERPLASTIC EPIDERMIS1021GRANULAR LAYER ABSENT1022THICKENED GRANULAR LAYER1031
WITH DERMAL GRANULOMA1032NECROBIOTIC COLLAGENOUS1033ELASTIC FIBERS AND DEBRIS10
4NECROTIZED AND INFLAMED1036HYPERKERATOTIC DILATATION1041WITH NO OTHER FINDINGS
1042PROJECTING ABOVE SURFACE1043IN AN ADULT1044WITH LARGE SEBACEOUS GLANDS1045
WITH FIBROSIS & INFLAMMATION105TWO LAYERS OF CELLS106CYTOPLASMIC VACUOLIZATION
107NONVACUOLATED PARAKERATOSIS106EPIDERMOLYTIC ACANTHOSIS108
AMONG NORMAL KERATINOCYTES109LOST EPIDERMAL STRATIFICATN33GRANULAR DEGENERATION
110SOLID BASALOID PROLIFERATION111BASALOID RETICULATION112
WITH ENDOKERATOTIC CYSTS113EPIDERMAL SQUAMOUS EDDIES106CYTOPLASMIC VACUOLIZATIC
106EPIDERMOLYTIC ACANTHOSIS112FOLLICULAR DIFFERENTIATION112
SEBACEOUS DIFFERENTIATION1141IN ISOLATED PALISADED BUDS1142
FENESTRATED PALE CELL SHELF1143PALISADED PALE CELL PROLIFN1144
SPONGELIKE EPITHELIAL SEPTACHONDRODERMATITIS HELICISINFLAMED EPIDERMAL NEVUS115
INTRAEPIDERMAL ONLY116ENDOPHYTIC NEOPLASMMOLLUSCUM CONTAGIOSUM110
OF BASALOID CELLS116OF ATYPICAL KERATINOCYTES142SEBACEOUS DIFFERENTIATION
1191PIGMENTED CLUBSHAPED BUDDING1192WITH LARGE MELANIN GLOBULES1193
VACUOLATED PIGMENTED CELLS120WITH DERMAL CELLULAR NESTS121
NO NEVUS CELLS IN CORIUM122DERMAL MELANOCYTIC NESTS123NO MELANOCYTES IN CORIUM
123INVOLVING FOLLICULAR WALLS128DERMAL NEVUS CELL NESTS124INTRAGRANULAR125
INTERCELLULAR EDEMA126BALLOONING39DERMAL PAPILLARY EDEMA1271
CAPILLARY DILATATION & POLYS1272THINNED EPIDERMIS1273ACANTHOSIS FOCAL EXOCYTOSI
1274SPONGIOSIS & EXOCYTOSIS1275VACUOLATED EPIDERMAL CELLS129INTRACORNEAL130
SUBCORNEAL131SUPRAPAPILLARY132UNILOCULAR133DYSKERATOTIC CLEFT134NONDYSKERATOTIC
135KERATINIZING136TWO NONCORNIFIED CELL LAYERS137CILIATED138
NUMEROUS TINY FOLLICLES139DILATED PILOSEBACEOUS UNIT140EXTENDING INTO THE DERMI
141NONSTRATIFIED SMALL CELLS1421AND SEVERAL FOLLICULAR DUCTS1422
WITH ONE BASALOID CELL LAYER1423MANY BASALOID CELL LAYERS1431
SUPERFICIAL COMMA EXTENSIONS1432DEEP NONBRANCHING STRANDS46
LARGE CELLULAR LOBULES1441CRIBRIFORM SIEVELIKE PATTERN1442
EMBEDDED IN FIBROTIC STROMA1443ASYMMETRIC NONCIRCUMSCRIBED1444
CLOVERLEAF BRANCHES1451SMALL KERATINIZING CYSTS1452SUPERFICIAL BRANCHED STRANDS
1453DEEP AND PLEOMORPHIC1461SMALL EVEN EPITHELIAL CELLS1462
LARGE PALE & SMALL DARK CELL1463EPIDERMOID CELLS1464LARGE CLEAR CELLS1465
WITH HYALINE SHEATH147CHIEFLY LYMPHO-HISTIOCYTIC148INCLUDING EOSINOPHILS149
INCLUDING NEUTROPHILS150MONOMORPHOUS MAST CELLS151WITH KERATINOCYTIC NECROSIS15
NO NECROTIC KERATINOCYTESPENICILLAMINE BLISTEREPIDERMOLYSIS DYSTROPHICA
HERPES GESTATIONISERYTHEMA MULTIFORME153IN SUPERFICIAL DISTRIBUTION154
AT ALL LEVELS OF THE CORIUM155PERIFOLLICULAR156DEEP AND CHIEFLY FOCAL157
DEEP AND CHIEFLY DIFFUSE66VESSEL WALL INFLAMMATION280GRANULOMATOUS158
SPINDLE CELLS159HISTIOCYTES160ATYPICAL HISTIOCYTES161PLEOMORPHIC CELLS162
ATYPICAL PLEOMORPHIC CELLS94LARGE GRANULAR CELLS150MONOMORPHOUS MAST CELLS95
ATYPICAL EPITHELIOID CELLS289MYOCYTIC1631SMALL EOSINOPHILIC GLOBULES1632
CLEFTED BASOPHILIC DEPOSITS1633BASOPHILIC ELASTOTIC FIBERS1634
SPICULE OF OSSIFIED BONE164IN THE EPIDERMIS AS WELL165MUCINOUS LAKES166
FIBROPLASTIC167PSEUDOCYSTIC168IN THE PAPILLARY CORIUM169IN THE RETICULAR CORIUM
170DENDRITIC SPINDLE SHAPED171ATYPICAL1721CONCENTRIC FIBROUS TISSUE1722
NETLIKE OUTER ROOT SHEATH1723MUCINOUS AROUND VESSELS1731HYPERKERATOTIC PAPILLAR
1732HYPERKERATOTIC RETICULAR1733HYALINISED BLOOD VESSELS1734
VELLOUS HAIR FOLLICLES358UNENCAPSULATED DERMAL NODULEMORPHEASCLERODERMA
PROGRESSIVE SYSTEM SCLEROSIS1741MATURE RETICULAR TISSUE1742
CELLULAR TISSUE NO ELAST C1743FIBRILAR PARALLEL TO SURFACE1744

THICK HYALINISED BUNDLES1745HYPERPLASTIC VASCULAR TISSUE1746
EXCESSIVE NUMBERS OF VESSELS358UNENCAPSULATED DERMAL NODULE1751
OVERABUNDANT ELASTIC FIBERS1752ABNORMAL SERRATED OUTLINES1753
BROKEN FRAYED RAVELED CURLED1761THICK CURLED CLUMPED FIBERS1762
AMORPHOUS HYPERPLASTIC MASS1763WITH DEPLETION OF COLLAGEN1764
CONFLUENT DILATED PAPILLAE1771BROKEN FRAYED CURLED RAVELED1772
HYPERPLASTIC NORMAL ELASTIC1773DUSTLIKE FRAGMENTED GRANULES178NON-NECROTIZING17
FIBRINOID VASCULITIS180NECROTISING VASCULITIS18110BLITERATED BY INFLAMMATION18J
WALL FRAYED AND INFILTRATED1813EOSINOPHILS & WALL NECROSIS1814
SUBPAPILLARY PLEXUS FIBRIN1815WITH LITTLE INFLAMMATION182TELANGIECTASIA183
LOBULES OF BLOOD VESSELS184LYMPHATIC VESSELS188VASCULAR SLITS MONONUCLEARS186
PERIVASCULAR INFLN& FIBROSIS185LOBULES OF SMALL VESSELS186
LYMPHOID WITH EOSINOPHILS187DILATED HYALINISED CHANNELS188
HEMORRHAGE AND INFLAMMATION
188SPINDLE CELLS VASCULAR SLITS189ENDOTHELIAL CELLS190PERICYTIC PROLIFERATION19
1SUBJACENT BAND OF INFILTRATE1912GIANT FIBROBLASTS & ECTASIA1913
LOSS OF CORIUM & FOLLICLES1914FIBROUS FOLLICULAR REMNANTS1921
SCAR DEVOID OF ADNEXA1922LOST RIDGES AND CAPILLARIES1923WITH EPIDERMAL ATROPHY
1924WITH MICROANGIOPATHY1925THIN EPIDERMIS AND DERMIS1926
DEEP DERMAL HYALINIZATION1927COMPLETE LOSS OF ELASTIC1928
LYMPHOHISTIOCYTIC INFILTRATE1931TANGLED AXON & SCHWANN CELLS1932
INTERMETATARSAL LOCATION1933TWO TYPES OF TISSUE74STREAMING ELONGATED NUCLEI1941
DELINEATED ORDERLY BUNDLES1942FASCICULAR ORGANOID PATTERN1943
FIBRILLAR WITH THICK VESSELS1944PACKED WAVY STREAMS OF CELLS1945
TWO TYPES OF TISSUE1951CELLULAR & RESEMBLING A MAT1952ATYPICAL NEVOID CELLULAR
1953STREAMING ELOGATED NUCLEI1954EOSINOPHILIC IN LOOSE TISSUE1955
CELL NESTS AND HYALINE DEGEN1961IN MYXOID VASCULAR STROMA1962
INFLAMED INFILTRATION OF FAT1963MULTINODULAR COLLAGEN1964
BRANCHING REFRACTILE FIBERS1965MULTINUCLEATED GIANT CELLS197BENIGN AND ORDERLY
198NUMEROUS MITOTIC FIGURES199MYXOID HISTIOCYTIC200ROUND NUCLEATED ROUND CELLS
201PLEOMORPHIC & INFLAMMATORY94LARGE GRANULAR CELLS95SMALL OVAL CELLS92MYOCYTIC
78SYNOVIAL LINING358UNENCAPSULATED DERMAL NODULE2021EOSINOPHILS & WALL NECROSIS
2022EXTRAVASCULAR GRANULOMATOUS2023SUBENDOTHELIAL PROLIFERATION2024
SURROUNDED BY NECROSIS2031WITHOUT VASCULITIS2032ORGANIZED SPARSELY INFLAMED203C
RECANALIZING THORACIC VEIN2034ORGANIZING & RECANALIZING2035
WITH SEVERE PANNICULITIS2036VESSEL WALL INFILTRATION204
HEMANGIOMA IN ADIPOSE TISSUE186NEW VESSELS WITH EOSINOPHILS187
DILATED HYALINISED CHANNELS189ENDOTHELIAL CELLS190PERICYTIC PROLIFERATION205
SPINDLE CELLS VASCULAR SLITS2061LARGE MUSCLE-COATED CISTERN2062
THICK-WALL TORTUOUS CHANNELS2063VESICLES FUSED TOGETHER2064
DILATED THICK-WALLED CYSTS207VASCULITIS208PANNICULITIS209VASCULITIS210
PANNICULITIS2111SCAR DEVOID OF ADNEXA2112DEEP SCLEROTIC INFLAMMATION2113
INFILTRATE AROUND VESSELS2114DISAPPEARED SUBCUTANEOUS FAT2121
LARGE GRANULAR FIBROBLASTS2122INFLAMED HYALINIZED NECROTIC2123
FAT HERNIATION INTO DERMIS2124TUMORLIKE OVERGROWING MASS2125
MULTINODULAR LIPOMATOSIS2126INFLAMMATORY SCLEROSIS219HYALINISED & EOSINOPHILIC
2131UNIFORM ADHERENT FAT CELLS2132MUCINOUS ELONGATED CELLS2133
SPIDER WEB SPINDLE CELLS2134BIZARRE MONSTER CELLS2135
VESSELS FIBROSIS & FAT CELLS2136WITH HEMATOPOIETIC ELEMENTS2137
VESSELS & FIBROMYOCYTE CELLS2138MULTINUCLEATE GRANULAR CELLS2141
VACUOLATED & GRANULAR CELLS2142CELLS WITH NOTCHED NUCLEUS2151
THICK BLOOD VESSEL WALLS2152BLOOD VESSELS & FAT CELLS2153
AND FIBROSIS BETWEEN BUNDLES2154TUMOR WITH MITOTIC FIGURES2161
CLOSE UNIFORM GRANULAR CELLS2162HAPHAZARD MESENCHYMAL STROMA2171
ADHERENT EOSINOPHILIC CELLS2172ORGANOID ALVEOLAR PATTERN2181MULTINODULAR2182
MYXOID STROMAACANTHOSIS NIGRICANSCONFLNT RETIC PAPILLOMATOSIS2291
WITH VASCULAR INFLAMMATION2292LITTLE DERMAL INFLAMMATIONICHTHYOSIS VULGARIS
X-LINKED ICHTHYOSISKYRLE'S DISEASEPERFORATING COLLAGENOSISELASTOSIS PERFORANS
PERFORATING FOLLICULITISTRANSEPITHELIAL ELIMINATIONKERATOSIS PILARIS
HYPERKERATOSIS PENETRANSAVITAMINOSIS A
KERATOSIS PILARISLICHEN SPINULOSISPHRYNODERMAPELLAGRAULERYTHEMA OPHRYOGENES
HYPERKERATOSIS PENETRANSAVITAMINOSIS A2301PLASMA CELLS VASCULAR STROMA2302
DEEP BRANCHING NIPPLE DUCTS2303SUBAREOLAR BRANCHING DUCTS231
BALLOONING GRANULAR CELLS232THICKENED GRANULAR LAYER233HYPERGRANULOTIC CELLS234
IN BROAD COLUMNS2342IN NARROW COLUMNS2343WITH ACTINIC ELASTOSISPAGET'S DISEASE
EXTRAMAMMARY PAGET'S DISEASE235POIKILOKARYOTIC DYSKERATOSIS236
DEMARCATED FROM ACANTHOSIS2371WITH ENDOKERATOTIC CYSTS2372
DEMARCATED FROM EPIDERMIS2381LACY PENETRATION OF DERMIS2382
PIGMENTED CLUB-SHAPED BUDSSEBORRHEIC KERATOSISPILAR SHEATH ACANTHOMA
TRICHOADENOMAHAIR FOLLICLE TUMORSIGN OF LESER-TRELATIRRITATED SEBORRH. KERATOSI
BASOSQUAMOUS CELL ACANTHOMASUPERFICIAL BASAL CELL CAFOLLICULAR INFUNDIBULUM TUM
TRICHILEMMOMAPINKUS FIBROEPITHELIAL TUMOR2391STRATIFICATION MAINTAINED2392
ENTIRE EPIDERMIS DERANGED2393GRANULAR DEGENERATION2401CENTRAL HORN-FILLED CRATE

2402PENETRATING RETICULAR CORIUMSYPHILISPLASMACYTOMAMULTIPLE MYELOMA
DERMAL MELANOSISINFLAMMATORY HYPERPIGMENTNHEMOSIDEROSISHEMOCHROMATOSISTATTOO
ACTINIC LENTIGONEVOID LENTIGOMELANOCYTIC HYPERPLASIA2431
WITHOUT INFLAMMATORY INFLN2432AND LYMPHOCYTIC INFILTRATION
JUNCTION MELANOCYTIC NEVUS2441INCLUDING PINK GLOBULES2442
HYPOCELLULAR & COLLAGENOUS2443LARGE NUCLEAR VARIATION2451
DERMAL ACTINIC ELASTOSIS2452NO ACTINIC ELASTOSISIMPETIGO
WEBER-COCKAYNE BULLOUS DERMEPIDERMOLYTIC HYPERKERATOSISPEMPHIGUS FOLIACEUS
STAPHYLOCOCCAL SCALDED SKINFRICTION BLISTER246KERATINOCYTIC NECROSIS247
HYPERPLASIA AND SPONGIOSIS248WITH LYMPHOCYTIC IMMIGRATION249
EOSINOPHILIC SPONGIOSIS250SUPERFICIAL INFILTRATION251DEEP DERMAL INFILTRATION25
LITTLE OR NO INFILTRATIONEARLY LESION OF PSORIASISPITYRIASIS LICHENOID CHRONIC
DIGITATE DERMATOSISPITYRIASIS ROSEAHERPETIC VIRAL LESIONB-K MOLE SYNDROME
FAMILIAL MALIGNANT MELANOMAPSORIASISCANDIDIASISDERMATOPHYTOSISCONTACT DERMATITI
IMPETIGINIZED DERMATITISPUSTULOSIS PALMARISPLANTARISSUBCORNEAL PUSTULAR DERM
IMPETIGOFUNGAL INFECTIONPUSTULAR PSORIASISMILIARIA CRYSTALLINA
CHRON GRANULOMATOUS DISEASEPEMPHIGUS FOLIACEUSPEMPHIGUS ERYTHEMATOSUS
FOGO SELVAGEMSTAPHYLOCOCCAL SCALDED SKINGUTTATE PSORIASISPUSTULAR PSORIASIS
ACRODERMATITIS CONTINUADERMATITIS REPENSCANDIDIASISREITERS DISEASEIODODERMA
SYPHILISDERMATOPHYTOSISBROMODERMAPUSTULOSIS PALMARISPLANTARISARTHROPOD BITE
SCABIESALLERGIC VASCULITISCHRONIC SEPTICEMIA2531SEVERAL FOCI & PARKERATOSIS253
ONLY ONE OR TWO FOCI2533WIDESPREAD2534DEEP FOLLICULAR INVOLVEMENT254
BENEATH THE CORNEAL LAYER255RETICULAR DEGENERATION257STRATIFIED SQUAMOUS LINING
258DARK-STAINED & SHADOW CELLS259DECAPITATION TYPE SECRETION2601
CUBOIDAL PAPILLARY LINING2602FLAT NUCLEATED CELL LININGBRONCHOGENIC CYST
CUTANEOUS CILIATED CYST
2611MATURE FIBROUS ROOT SHEATH2612ENTERING KERATINIZED SINUS2613
STRATIFIED KERATINIZED CYSTS2621CYSTIC ATROPHY OF THE WALL2622
PROLIFERATIVE ROOT SHEATH2623SUPERFICIAL ORS PROLIFERATN2631
INCLUDING SQUAMOUS EDDIES2632PALE CELLS WITH PALISADING2633
APOCRINE TYPE EPITHELIUMPILOMATRIXOMACALCIFYING EPITHELIOMA
NEVUS SEBACEUS OF JADASSOHNSEBACEOUS HYPERPLASIASEBACEOUS EPITHELIOMA
SEBACEOUS CARCINOMASYRINGOMAERUPTIVE HIDRADENOMASECONDARY CARCINOMA
BENIGN SWEAT GLAND TUMORECCRINE SPIRADENOMATRICHOEPITHELIOMA
DESMOPLASTIC TRICHOEPITHELIOBASAL CELL CARCINOMATRICHOFOLLICULOMATRICHOBLASTOMA
DESMOPLASTIC SYRINGOMASCLEROSING HAMARTOMACYLINDROMADESMOPLAST TRICHOEPITHELIOM
MORPHEALIKE BASAL CELL CASECONDARY CARCINOMAPRIMARY SWEAT GLAND CASYRINGOMA
ECCRINE DERMAL DUCT TUMORECCRINE SPIRADENOMANODULAR HIDRADENOMA
CLEAR CELL HIDRADENOMACUTANEOUS CYLINDROMAECCRINE ACROSPIROMAADNEXAL HAMARTOMA
PRIMARY MUCINOUS ECCRINE CACHONDROID SYRINGOMASECONDARY CARCINOMA264
AROUND SUPERFICIAL VESSELS265AT ALL LEVELS OF THE CORIUMCICATRICIAL PEMPHIGOID
BULLOUS PEMPHIGOIDINSECT BITE OR STINGHERPES GESTATIONISDERMATITIS HERPETIFORMI
DRUG ERUPTIONVESICULAR DISEASE CHILDHOODLUPUS ERYTHEMATOSUSERYSIPELAS
ERYTHROPOIETIC PROTOPORPHYRIACICATRICIAL PEMPHIGOIDURTICARIAURTICARIA PIGMENTOS
MAST CELL NEVUSTELANGIECTASIA ERUPTIVA PERSSYSTEMIC MASTOCYTOSIS
TOXIC EPIDERMAL NECROLYSISERYTHEMA MULTIFORMEDRUG ERUPTIONEPIDERMOLYSIS BULLOSA
PORPHYRIA CUTANEA TARDABULLOUS PEMPHIGOIDTHERMAL BURNTRAUMATIC BLISTER266
PROMINENT EPIDERMAL CHANGES267CHANGES CHIEFLY IN CORIUM333
OBSCURING THE INTERFACE269WITH EPIDERMAL CHANGES270INVOLVING THE INTERFACE271
CHIEFLY PERIVASCULAR155PERIFOLLICULAR361ATYPICAL LYMPHOID INFILTRATE272
INCLUDING POLYMORPHONUCLEARS273PREDOMINANTLY LYMPHOCYTIC274
HISTIOCYTIC & GRANULOMATOUS275SCARRING AND INFLAMMATORY355
CELLS WITH FOAMY CYTOPLASM277NEUTROPHILIC NONSUPPURATIVE278MATURE LYMPHOID279
ATYPICAL LYMPHOID280HISTIOCYTIC & GRANULOMATOUS282EOSINOPHILS AND HISTIOCYTES2
EOSINOPHILS AND HISTIOCYTES278MATURE LYMPHOID283PLEOMORPHIC LYMPHOID284
PLASMA CELLS285MATURE HISTIOCYTIC286LARGE ATYPICAL MONONUCLEARS150
MONOMORPHOUS MAST CELLS281INCLUDING NEUTROPHILS276SUPPURATIVE288NEUROCYTIC289
MYOCYTIC290FIBROCYTIC2911INFILTRATING AMONG COLLAGEN2912
TOUTON MULTINUCLEATED CELLS2913BIZARRE GIANT CELLS2921FOAM CELLS AND GIANT CELL
2922SHOWING PHAGOCYTIC ACTIVITY2923NODULES OF FUSIFORM CELLS2924
MASSED LARGE STELLATE CELLS2931BIZARRE DYSPLASTIC POLYGONAL2932
PERIVASCULAR ROUND CELLSMALIGNT FIBROUS HISTIOCYTOMACUTANEOUS AMYLOIDOSIS
COLLOID MILIUMACTINIC ELASTOSISOSTEOMA CUTISGARGOYLISMHUNTER-HURLER SYNDROME
MYXEDEMAPRETIBIAL MYXEDEMAACROMEGALYLICHEN MYXEDEMATOSISPAPULAR MUCINOSIS
SCLEROMYXEDEMAACROMEGALYSYNOVIAL CYSTGANGLIONMUCINOUS CYSTSALIVARY CYST2941
JUNCTIONAL MELANOCYTIC NESTS2942NO JUNCTION MELANOCYTE NESTS
INTRADERMAL NEVOCYTIC NEVUSCONGENITAL NEVUS2961SPARSELY SCATTERED CELLS2962
GROUPS WITHIN FIBROUS NODULE2963JUNCTIONAL MELANOCYTIC NESTS2964
BENIGN SCHWANNOMATOUS CELLS2965ATYPICAL MITOTIC ACTIVITYSPITZ NEVUS
MALIGNANT MELANOMA
PERIFOLLICULAR FIBROMAFIBROFOLLICULOMATRICHODISCOMAACROCHORDON
ACQUIRED FIBROKERATOMAFIBROEPITHELIAL PAPILLOMAANGIOFIBROMA
FIBROUS PAPULE OF FACEPEARLY PENILE PAPULECONNECTIVE TISSUE NEVUSFIBROUS PAPULE

SCARKELOIDTUBEROUS SCLEROSISANGIOFIBROMAEARLY PENILE PAPULESELASTOSIS PERFORAN
PENICILLAMINE EFFECTPSEUDOXANTHOMA ELASTICUMACTINIC ELASTOSISCUTIS RHOMBOIDALIS
ERYTHEMA AB IGNECOLLOID MILIUMPSEUDOXANTHOMA ELASTICUMNEVOID ELASTOMACUTIS LAXA
297NEUTROPHIL LEUCOCYTOCLASIA298INFILTRATE OF NEUTROPHILS299
LYMPHOCYTIC INFILTRATE300GRANULOMATOUS REACTION301ACELLULAR3021
WITH EPIDERMAL SPONGIOSIS3022WITH OCCLUSION OF LUMENA3023
INFLAMED WALL INFILTRATION3024DEEP AND GRANULOMATOUS3025
NEUTROPHILS AND EOSINOPHILS3026OCCLUSION AND HYALINIZATION3031
HYALIN LEUCOCYTIC INFILTRATE3032FRAGMENTED NUCLEAR DUST3033
ACUTE & CHRONIC INFLAMMATION3034NEUTROPHILS AND EOSINOPHILS3035
ORGANISMS IN VESSEL WALLS3036WITH PURPURIC HEMORRHAGEPERNIOSIS
THROMBOANGIITIS OBLITERANSPOLYARTERITIS NODOSADISSEMINATED IV COAGULATION
DYSPROTEINEMIAPAROXYSMAL HEMOGLOBINEMIAEMBOLISMCOUMARIN NECROSIS
ESSENTIAL TELANGIECTASIAOSLER'S FAMILIAL HEMORRHAGICNEVUS ARANEUS
ANGIOMA SERPIGINOSUMURTICARIA PIGMENTOSA3041SMALL THIN-WALLED LUMENS3042
LARGE THICK FIBROUS WALLED3043IMMATURE CAPILLARY PROLIFERN3044VENOUS LAKE3045
WITH REACTIVE HYPERKERATOSIS3046THICK WALL & FIBROUS STROMA
LYMPHANGIOMA CIRCUMSCRIPTUMGRANULOMA PYOGENICUMANGIOLYMPHOID HYPERPLASIA
CIRSOID ANEURYSMANGIOLYMPHOID HYPERPLASIAKIMURA'S DISEASE
ATYPICAL PYOGENIC GRANULOMAPAPULAR ANGIOPLASIAEOSINOPHILIC GRANULOMA
ANGIODERMATITISANGIOMATOSISARTERIOVENOUS FISTULAARTERIOVENOUS MALFORMATION
ARTERIOVENOUS FISTULACIRSOID ANEURYSMVASCULAR HAMARTOMARACEMOSE ANEURYSM3051
CONSPICUOUS INFLAMMATION3052PROMINENT VASCULAR COMPONENT3061
INTRALUMEN ENDOTHELIAL TUFTS3062PROFUSECAPILLARY ENDOTHELIUM3063
ATYPICAL CELLS LINING SPACES3064FIBROCYTIC VASCULAR SLITS3065
IRREGULAR DILATED THROMBOSED3066LOBULATED CAPILLARY LUMENS3067
PROLIFERATING ENDOTHELIUM3068PROLIFERATING PERICYTES3071
SOLID MASSED CUBOIDAL CELLS3072DYSCHONDROPLASIA ASSOCIATED3073
MITOTIC NECROTIC HEMORRHAGICLICHEN SCLEROSUS ATROPHICUSCHRONIC X-RAY DERMATITIS
SCARRING ALOPECIAPSEUDOPELADECHEMOTHERAPYTOXIC EFFECTCONGENITAL APLASIA
SENILE ATROPHYCORTICOSTEROID ATROPHYDIABETIC ATROPHYPASINI-PIERINI ATROPHODERMA
PROGYRIAANETODERMAACRODERMATITIS ATROPHICANSTRAUMATIC NEUROMAMORTON'S NEUROMA
NEURILEMMOMANEUROFIBROMAPLEXIFORM NEUROMAANGIONEUROMASCHWANNOMANEURILEMMOMA
DESMOID TUMORLEIOMYOMASTORIFORM SCHWANNOMAEPITHELIOID SCHWANNOMANEURILEMMOMA
GLIOMACUTANEOUS MENINGIOMAMYXOID NEUROFIBROMANEURONEVUSLEIOMYOMA
FIBROUS HISTIOCYTOMASCLEROSING HEMANGIOMAFASCIITISFIBROMATOSISCOLLAGENOMA
ELASTOFIBROMAGIANT CELL TUMOR3081INNER MYXOID CLEFTS & VILLI3082
SPINDLE CELLS IN SPIDER WEB3083ANGIOMATOUS IN MYXOID STROMA3084
DEFINED SPINDLE CELL TANGLES3085PLEOMORPHIC WITH GIANT CELLS3091
MONOMORPHOUS FIBROCYTIC3092CELLULAR UNIFORM HERRINGBONE3093
PLEOMORPHIC WITH GIANT CELLS3101ATYPICAL AMID FIBROUS TISSUE3102
WITH FORMATION OF CAVITY3103MUCINOUS & RETICULAR LAYERS3111
FIBROBLASTIC AND HISTIOCYTIC3112MACROPHAGES AND FOAMY CELLS3113
LARGE MULTINUCLEATED CELLS3114PALE CELLS PROMINENT NUCLEI3121
FIBROBLASTS AND FOAM CELLS3122HISTIOCYTIC & GRANULOMATOUS3123
DISORDERLY BIZAR GIANT CELLS3124MYOCYTICPOLYARTERITIS NODOSA
ANGIOCENTRIC GRANULOMATOSISGIANT CELL ARTERITISWEGENER'S GRANULOMA
ALLERGIC GRANULOMATOSISPHLEBOTHROMBOSISVARICOSE THROMBOPHLEBITISMONDOR'S DISEAS
SCLEROSING LYMPHANGIITISNODULAR VASCULITISMIGRATORY THROMBOPHLEBITIS
MIGRATORY PANNICULITISANGIOLIPOMAANGIOFIBROLIPOMAKAPOSI'S SARCOMA
IDIOPATHIC HEMORRHAGIC SARC.STEWART-TREVES SYNDROMELYMPHANGIOSARCOMA
LYMPHANGIOMALYMPHANGIOMYOMALYMPHATIC CYSTCYSTIC HYGROMAHEMANGIOMA
LYMPHANGIOSARCOMA3131INFILTRATE WITHIN THE WALL3132INFLAMED NECROSIS OF VESSEL
3133FIBRINOID ROUND CELL INFILTR3141NEUTROPHILS INVADING LOBES3142
WITH SCLEROSIS OF FASCIA3151INFLN & ENDOTHELIAL SWELLING3152
INFILTRN OBLITERATING VESSEL3161INFILTRATED & CLEFTED SPACES3162
GRANULAR BASOPHILIC LIPOCYTE3163PATCHY CLEFTS AND FOAM CELLS3164
WITH LIQUIFACTION NECROSIS3165GRANULOMATOUS AND FIBROSED3166
WITH EPITHELIOID TUBERCLES3167DISAPPEARANCE OF FAT TISSUE210
CYTOPHAGIC HISTIOCYTESAPLASIA CUTIS CONGENITACENTRIFUGAL LIPODYSTROPHY
PROGRESSIVE LIPODYSTROPHYSECONDARY TO INSULIN INJECTNGOWER'S PANATROPHY
FAT NECROSISSCLEROSING LIPOGRANULOMAPIEZOGENIC PAPULESADIPOSIS DOLOROSA
STEATOPYGIALIPODYSTROPHYLIPOMAMYXOID LIPOMAFIBROLIPOMAHIBERNOMAANGIOLIPOMA
ANGIOMYOLIPOMAMYELOLIPOMALIPOGRANULOMALIPOBLASTOMALIPOSARCOMAMYXOMAFIBROMATOSIS
MYXOID LIPOSARCOMAEMBRYONAL RHABDOMYOSARCOMAANGIOMYOMAANGIOMYOLIPOMALEIOMYOMA
LEIOMYOSARCOMADESMOID TUMORANGIOFIBROMABENIGN SCHWANNOMARHABDOMYOMA
FETAL RHABDOMYOMAGRANULAR CELL MYOBLASTOMAGRANULAR CELL MYOBLASTOMA
ALVEOLAR SOFT PART SARCOMAADNEXAL CARCINOMASECONDARY ADENOCARCINOMARHABDOMYOMA
PARAGANGLIONOMALEIOMYOSARCOMAEPITHELIOID SARCOMACHORDOID SARCOMA
NERVE SHEATH MYXOMANEUROTHEKOMAFASCIITISFIBROMATOSISGRANULOMACLEAR CELL SARCOMA
LIPOSARCOMALUPUS ERYTHEMATOSUS PROFUNDUPANCREATIC PANNICULITISPARAFFINOMA
CHONDRODERMATITIS HELICISVERRUCOUS EPIDERMAL NEVUSEPIDERMOLYTIC ACANTHOMA

SYRINGADENOMA PAPILLIFERUMEROSIVE ADENOMATOSISFLORID PAPILLOMATOSIS
VERRUCA VULGARISVERRUCA PLANTARIS319RETICULATION OF EPIDERMIS320
EPIDERMIS NOT RETICULATED319GRANULAR DEGENERATION3211HYPERKERATOTIC3212
ORTHOKERATOTICINFLAMED EPIDERMAL NEVUSPOROKERATOSISACTINIC POROKERATOSIS
EPIDERMAL DYSPLASIABOWEN'S DISEASEBOWENOID PAPULOSISERYTHROPLASIA OF QUEYRAT
CARCINOMA IN SITUPALE CELL ACANTHOMASEBORRHEIC KERATOSISECCRINE POROMA
VERRUCOUS CARCINOMAMELANOACANTHOMAINVERT FOLLICULAR KERATOSISTRICHILEMMOMA
BENIGN ADNEXAL TUMORSEBORRHEIC KERATOSISACTINIC LENTIGOACTINIC KERATOSIS
BOWEN'S DISEASEEPIDERMOLYTIC ACANTHOMACUTANEOUS HORN
KERATOACANTHOMASQUAMOUS CELL CARCINOMAEPITHELIOMA CUNICULATUMVERRUCOUS CARCINOM
COMPOUND NEVUSHALO NEVUSIRRITATED NEVUSSPITZ NEVUSDESMOPLASTIC NEVUS
MALIGNANT MELANOMALENTIGO MALIGNADYSPLASTIC NEVUSATYPICAL MELANOCYTIC HYPERPL
B-K MOLE SYNDROMEMELANOMA IN SITUSPITZ NEVUSPRIMARY IRRITANT CONTACT DERM
PHOTODERMATITISPHYTOPHOTOCONTACT DERMATITISERYTHEMA MULTIFORMECONTACT DERMATITI
NUMMULAR ECZEMADYSHIDROSISID REACTIONPITYRIASIS LICHENOIDES ACUTA322
SUPERFICIAL INFILTRATE ONLY323DEEP INFLAMMATORY INFILTRATE324
SUPERFICIAL INFILTRATE ONLY325DEEP INFLAMMATORY INFILTRATEVIRAL VESICLE
PHOTODERMATITISMILKER'S NODULECONTACT DERMATITISECTHYMA CONTAGIOSUM
HAND FOOT MOUTH DISEASEERYTHEMA MULTIFORMEIMMERSION FOOTPACHYONYCHIA CONGENITA
NECROLYTIC MIGRATORY ERYTHGLUCAGONOMA BULLOUS DERMPELLAGRA
ACRODERMATITIS ENTEROPATHICFIXED DRUG ERUPTIONPITYRIASIS LICHENOIDES ACUTA
PHOTOCONTACT DERMATITISICHTHYOSIFORM ERYTHRODERMAEPIDERMOLYTIC HYPERKERATOSIS
ICHTHYOSIS HYSTRIXLAMELLAR ICHTHYOSISDARIER'S DISEASEGROVER'S DISEASE
HAILEY DISEASEWARTY DYSKERATOMAACANTHOLYTIC SQUAMOUS CELL CPEMPHIGUS VULGARIS
PAGET'S DISEASEPEMPHIGUS FOLIACEUSPEMPHIGUS ERYTHEMATOSUSFOGO SELVAGEMIMPETIGO
STAPH SCALDED SKIN SYNDROMEHERPES SIMPLEXZOSTERVARICELLACANTHARIDIN BLISTER
BEETLE BLISTERACUTE VESICULAR DERMATITISPEMPHIGUS VULGARISPEMPHIGUS VEGETANS
HAILEY'S DISEASEDARIER'S DISEASEGROVER'S DISEASE3261PALE CELLS NO GRANULAR LAYE
3262PROLIFERATED FOLLICLE SHEATH3263GRANULAR LAYER PRESENT3264
CONTAINING VELLUS HAIR COIL3265CUTANEOUS ADNEXA IN THE WALL3266
LYMPHOID STRUCTURES IN WALLPILOMATRICOMACALCIFYING EPITHELIOMA3271
PAPILLARY & TRABECULATED3272DILATED TUBULAR STRUCTURES3273
PAPILLAE PROJECT INTO SPACESPAPILLARY ECCRINE ADENOMAECCRINE HIDROCYSTOMA
CHONDROID SYRINGOMAMIXED TUMOR OF SKINHAIR FOLLICLE NEVUSTRICHOFOLLICULOMA
TRICHOADENOMANEVUS COMEDONICUSPILAR SHEATH ACANTHOMAWINER PORE
INVERT FOLLICULAR KERATOSISTRICHILEMMOMAAPOCRINE CYSTADENOMA
SYRINGCYSTADENOMA PAPILLIFER328IN A SUB-EPIDERMAL BAND329WITH VACUOLAR CHANGES
POLYMORPHOUS LIGHT ERUPTION330PSORIASIFORM HYPERPLASIA331INTERCELLULAR EDEMA33
HYPERPLASIA AND SPONGIOSIS266EXOCYTOSIS INTO EPIDERMIS333
AT THE EPIDERMAL INTERFACE334PERIVASCULAR & INTERSTITIAL335
PERIFOLLICULAR LOCALIZATION336PSORIASIFORM HYPERPLASIA337INTERCELLULAR EDEMA36
ATYPICAL EPIDERMAL CELLS361ATYPICAL LYMPHOID INFILTRATE338LYMPHOHISTIOCYTIC339
MIXED INFLAMMATORY CELLS361ATYPICAL LYMPHOID INFILTRATE340LYMPHOCYTIC341
INCLUDING NEUTROPHILS342INCLUDING EOSINOPHILS343MIXED CELL INFILTRATION286
HISTIOCYTICFURUNCLECARBUNCLESYCOSIS BARBAEFOLLICULITIS DECALVANSTINEA BARBAE
MAJOCCHI'S GRANULOMAFAVUSKERIONACNE CONGLOBATAHIDRADENITIS SUPPURATIVA
DISSECTING CELLULITISROSACEAIODODERMABROMODERMAULERYTHEMA OPHYOGENES
LICHEN SPINULOSUSLICHEN PLANOPILARISDISCOID LUPUS ERYTHEMATOSUSSCURVY
ALOPECIA AREATATHALLIUM EFFECT
ACNEROSACEAPERIORAL DERMATITISOIL FOLLICULITISSTEROID FOLLICULITIS
PSEUDOFOLLICULITISIODODERMABROMODERMABOCKHART'S IMPETIGOCANDIDIASIS
DERMATOPHYTOSISSECONDARY SYPHILIS344REPLACING THE HAIR FOLLICLES345
DIFFUSE THRUOUT THE DERMISDEEP FUNGAL INFECTIONATYPICAL MYCOBACTERIAL
ACTINOMYCOSISNOCARDIOSISMYCETOMACAT SCRATCH DISEASETULAREMIA
LYMPHOPATHIA VENEREUMIODODERMABROMODERMACHALAZIONABSCESSSWEET'S SYNDROME
ACUTE FEBRILE NEUTROPHILIC DERMCHALAZIONGRANULOMA FACIALE
ERYTHEMA ELEVATUM DIUTINUMPSEUDOLYMPHOMASPIEGLER-FENDT SARCOID
LYMPHADENOSIS BENIGNA CUTISLYMPHOCYTOMA CUTISLYMPHOMATOID PAPULOSIS
ARTHROPOD BITE OR STINGRUPTURED HAIR FOLLICLEGIANNOTTI-CROSTI SYNDROME
MYCOSIS FUNGOIDESFOLLICULAR LYMPHOMANODULAR LYMPHOSARCOMA276
EOSINOPHILS AND NEUTROPHILS346EPITHELIOID CELL TUBERCLES347
PALISADING AND NECROBIOTIC348CONTAINING FOREIGN MATERIALGRANULOMA FACIALE
ERYTHEMA ELEVATUM DIUTINUMPYODERMA GANGRENOSUMCELLULITISERYSIPELASANTHRAX
SWEET'S SYNDROMEINSECT BITEWELL'S SYNDROMEEOSINOPHILIC CELLULITIS349
MONOMORPHOUS LYMPHOCYTIC350POLYMORPHOUS351WITH ULCERATION OF EPIDERMIS352
WITHOUT EPIDERMAL ULCERATION353MONONUCLEAR CELLS291MULTINUCLEATED GIANT CELLS35
CELLS WITH FOAMY CYTOPLASMHISTIOCYTOSIS XLETTERER-SIWE DISEASE
HAND-SCHULLER-CHRISTIANLYMPHOMATOID PAPULOSISLYMPHOMATOID GRANULOMATOSIS
RETICULOSISHISTIOCYTIC SARCOMAMONOCYTIC LEUKEMIAXANTHOMA DISSEMINATUM
B OR T CELL LYMPHOMA73HYPERPLASTIC CONGLOMERATION75NONCOLLAGENOUS CELLULAR3571
LINEAR INTERSECTING BUNDLES3572ATYPICAL AND MITOTIC CELLS3573
STRIATED CYTOPLASMIC CELLS358CELLS DENSE BETWEEN FIBERS359
MUCINOUS BETWEEN FIBERSBENIGN FIBROUS HISTIOCYTOMAJUVENILE XANTHOGRANULOMA

RETICULOHISTIOCYTE GRANULOMAHISTIOCYTOSIS XMALIGNANT HISTIOCYTOSIS
MALIGNT FIBROUS HISTIOCYTOMARETICULUM CELL SARCOMAATYPICAL FIBROXANTHOMA
BENIGN FIBROUS HISTIOCYTOMACOMPOUND NEVUSINTRADERMAL NEVOCYTIC NEVUSHALO NEVUS
EPITHELIOID CELL NEVUSB-K MOLENEVUS OF OTABLUE NEVUSCOMBINED NEVUS
CELLULAR BLUE NEVUSMALIGNANT MELANOMAMELANOTIC NEUROFIBROMA
HENOCH-SCHONLEIN PURPURAERYTHEMA ELEVATUM DIUTINUMGRANULOMA FACIALE
DRUG-INDUCED REACTIONALLERGIC VASCULITISMACROGLOBULINEMIALUPUS ERYTHEMATOSUS
LEUKOCYTOCLASTIC VASCULITISSEPTICEMIAMENINGOCOCCEMIAGONOCOCCEMIA
SYPHILITIC VASCULITISPITYRIASIS LICHENOIDES ACUTALYMPHOMATOID PAPULOSIS
GRANULOMA ANNULARENECROBIOSIS LIPOIDICAMIESCHER'S GRANULOMA
ANGIOCENTRIC GRANULOMATOSISALLERGIC GRANULOMALYMPHOMATOID GRANULOMADEGOS DISEAS
MALIGNANT ATROPHIC PAPULOSISLIVEDO VASCULITISATROPHIE BLANCHESTASIS DERMATITIS
ATROPHIE BLANCHEALLERGIC ANGIITISLUPUS ERYTHEMATOSUS PROFUNDU
ERYTHEMA ELEVATUM DIUTINUMLIVEDOID VASCULITISDYSPROTEINEMIC PURPURA
GRANULOMA FACIALENECROBIOSIS LIPOIDICAALLERGIC VASCULITIS
LEUKOCYTOCLASTIC VASCULITISPOLYARTERITIS NODOSAERYTHEMA ELEVATUM DIUTINUM
KAWASAKI'S DISEASEHENOCH-SCHONLEIN PURPURADERMATOSIS NECROTICA NODULAR
CAPILLARY HEMANGIOMACAVERNOUS HEMANGIOMAJUVENILE HEMANGIOMASENILE VARIX
ANGIOKERATOMACIRSOID ANEURYSMBLUE RUBBER BLEB NEVUSPYOGENIC GRANULOMA
KAPOSI'S SARCOMAHEMORRHAGIC INFLAMED SCARACQUIRED IMMUNE DEFICIENCY S
PAPILLARY ENDOTHELIAL HYPRPLANGIOMATOSISANGIOSARCOMAKAPOSI'S SARCOMA
THROMBOSED VARIXPYOGENIC GRANULOMALYMPHANGIOSARCOMAHEMANGIOPERICYTOMA
GLOMUS TUMORKAST-MAFFUCI SYNDROMEHEMANGIOPERICYTOMA
SYNOVIAL CYSTFIBROLIPOMANEUROFIBROMAATYPICAL FIBROXANTHOMADESMOID TUMOR
FIBROBLASTIC FIBROSARCOMAPLEOMORPHIC FIBROSARCOMAFIBROUS HISTIOCYTOMA
SYNOVIAL CYSTMYXOMABENIGN SCHWANNOMAMYXOID HISTIOCYTOMALIPOBLASTOMA
SCLEROSING LIPOMAFASCIITISFIBROUS HISTIOCYTOMAGIANT CELL TUMOR
RETICULOHISTIOCYTE GRANULOMACLEAR CELL SARCOMAPLEOMORPHIC LIPOMA
PLEOMORPHIC LIPOSARCOMAREPARATIVE GRANULOMAXANTHOMAFIBROUS HISTIOCYTOMA
ATYPICAL FIBROXANTHOMAGRANULAR CELL MYOBLASTOMAPLEOMORPHIC LIPOMAFIBROSARCOMA
LEIOMYOMALEIOMYOSARCOMATENOSYNOVIAL SARCOMANONCOLLAGENOUS SCHWANNOMA
MIGRATORY THROMBOPHLEBITISPOLYARTERITIS NODOSALUPUS ERYTHEMATOSUS PROFUNDU
ERYTHEMA NODOSUMEOSINOPHILIC FASCIITISNODULAR VASCULITISFERNIOSISCHILBLAIN
ERYTHEMA INDURATUMSCLEREMA NEONATORUMPANCREATIC PANNICULITIS
CORTICOSTEROID INJECTIONWEBER-CHRISTIAN DISEASESCLEROSING LIPOGRANULOMA
SARCOIDOSISLIPODYSTROPHYTRAUMATIC FAT NECROSISERYTHEMA NODOSUM LEPROSUM
CYTOPHAGIC PANNICULITISLUPUS ERYTHEMATOSUS PROFUNDSHEREDITARY KERATODERMA
ICHTHYOSIFORM ERYTHRODERMAEPIDERMOLYTIC HYPERKERATOSISICHTHYOSIS HYSTRIX
ACTINIC KERATOSISEPIDERMOLYTIC ACANTHOMALINEAR EPIDERMAL NEVUSVERRUCA PLANA
EPIDERMODYSPLASIA VERRUCIFRMVERRUCA VULGARISCONDYLOMA ACCUMINATA
CONTACT DERMATITISNUMMULAR ECZEMAID REACTIONDYSHIDROSISDERMATOPHYTOSIS
PHOTOALLERGIC CONTACT DERMATITISHYDROA VACCINIFORMEARTHROPOD BITE OR STING
INCONTINENTIA PIGMENTIPEMPHIGUS VULGARISPEMPHIGOIDHERPES GESTATIONIS
CONTACT DERMATITISARTHROPOD BITE OR STINGSCABIESLARVA MIGRANSCREEPING ERUPTION
CERCARIAL DERMATITISSWIMMER'S ITCHPAPULAR URTICARIATRICHILEMMAL CYST
PROLIFERATING CYSTEPIDERMOID CYSTERUPTIVE VELLUS HAIR CYST
STEATOCYSTOMA MULTIPLEXBRANCHIAL CLEFT CYSTDERMOID CYSTINFUNDIBULAR CYSTMILIUM
HIDRADENOMA PAPILLIFERUMTUBULAR APOCRINE ADENOMAAPOCRINE CYSTADENOMA
LICHEN PLANUSLICHEN SCLEROSUS ATROPHICUSERYTHEMA MULTIFORME
TOXIC EPIDERMAL NECROLYSISLICHEN SCLEROSUS ATROPHICUSPSORIASISNEURODERMATITIS
CONTACT DERMATITISECZEMAINCONTINENTIA PIGMENTIPITYRIASIS RUBRA PILARIS
CANDIDIASISDERMATOPHYTOSISPELLAGRALAMELLAR ICHTHYOSISPARAPSORIASIS
ACRODERMATITIS ENTEROPATHICAINFLAMED LINEAR NEVUS363SPONGIOSIS364
EOSINOPHILIC SPONGIOSIS332HYPERPLASIA AND SPONGIOSISNUMMULAR ECZEMA
CONTACT DERMATITISSEBORRHEIC DERMATITISPARAPSORIASISPREMYCOTIC MYCOSIS FUNGOIDE
GRAFT VERSUS HOST REACTION365VACUOLAR AND VESICULAR366IN A SUB-EPIDERMAL BAND37
GRANULOMATOUS362ATYPICAL EPIDERMAL CELLS367LYMPHOHISTIOCYTIC368
INCLUDING SOME LEUKOCYTES150MONOMORPHOUS MAST CELLS369WITH FOLLICULAR MUCINOSIS
370WITH FOLLICULAR SPONGIOSISSCABIESSECONDARY SYPHILISACTINIC RETICULOID
PITYRIASIS ROSEAPHOTODERMATITISARTHROPOD REACTIONFIXED DRUG ERUPTION
DERMATOPHYTOSISCELLULITISPITYRIASIS LICHENOIDES ACUTADISCOID LUPUS ERYTHEMATOSI
PITYRIASIS LICHENOIDES ACUTAPHOTODERMATITISERYTHEMA ELEVATUM DIUTINUM
DERMATOPHYTOSISPOLYMORPHOUS LIGHT ERUPTIONLYMPHOMATOID PAPULOSIS
MYCOSIS FUNGOIDESFIXED DRUG ERUPTIONSECONDARY SYPHILISLYMPHOCYTIC INFILTRATION
ERYTHEMA ANNULARE CENTRIFUGUMALLERGIC VASCULITISEARLY SCLERODERMA
POLYMORPHOUS LIGHT ERUPTIONLUPUS ERYTHEMATOSUSDERMATOMYOSITISCELLULITIS
ERYSIPELASACUTE FEBRILE NEUTROPHILIC DERMSWEET'S SYNDROME
ERYTHROPOIETIC PROTOPORPHYRIAARTHROPOD BITEALLERGIC VASCULITIS
ARTHROPOD BITE OR STINGSWEET'S SYNDROMEHERPES GESTATIONISBULLOUS PEMPHIGOID
FOREIGN BODY REACTIONPSEUDOLYMPHOMALYMPHOMATOID PAPULOSISMYCOSIS FUNGOIDES
GRANULOMA FACIALETREATED LYMPHOMAURTICARIADRUG-INDUCED ERUPTION
ARTHROPOD BITE OR STINGALLERGIC REACTIONSCARRING ALOPECIAGRAHAM-LITTLE SYNDROME
PSEUDOPELADEFIBROSING ALOPECIAPOSTINFLAMMATORY ALOPECIACHRONIC RADIODERMATITIS

HEALED ULCERHEALED BURNSCAR375CASEATING GRANULOMA376NONCASEATING GRANULOMA
GRANULOMA ANNULARENECROBIOSIS LIPOIDICARHEUMATIC NODULERHEUMATOID NODULE
MIESCHER'S GRANULOMABERYLLIUM GRANULOMATRAUMATIC NECROBIOSIS
INJECTABLE COLLAGEN IMPLANTFOREIGN BODY GRANULOMADISRUPTED TRICHILEMMAL CYST
LYMPHOCYTIC LYMPHOMALEUKEMIA CUTISDIFFUSE LYMPHOSARCOMA377EPIDERMOTROPIC378
NON-EPIDERMOTROPICPRIMARY SYPHILISCHANCROIDGRANULOMA INGUINALE
LYMPHOPATHIA VENEREUMLEISHMANIASISRHINOSCLEROMASECONDARY SYPHILISPLASMACYTOMA
HISTOPLASMOSISLEISHMANIASISHISTIOCYTOMAXANTHOMAHISTIOCYTOMALEPROMATOUS LEPROSY
SCLEROSING LIPOGRANULOMAGIANT CELL TUMORLEIOMYOMALEIOMYOSARCOMARHABDOMYOMA3811
PHAGOCYTIC OF PIGMENT3812INTERLACING COLLAGEN BUNDLES3813
FIBROBLASTS AND CAPILLARIES3814CARTWHEEL FASCICLESSYNOVIAL CYSTSCLEROMYXEDEMA
ATYPICAL LYMPHOID INFILTRATEREACTIVE LYMPHOID HYPERPLASI
LYMPHOMATOID GRANULOMATOSISHODGKIN'S DISEASEWEGENER'S GRANULOMA
FOLLICULAR LYMPHOMAEPITHELIOID SARCOMAERYTHEMA MULTIFORMEHERPES SIMPLEX
LUPUS ERYTHEMATOSUSMYCOSIS FUNGOIDESCONTACT DERMATITISPHOTODERMATITIS
ECZEMATOUS DERMATITISID REACTIONDYSHIDROSISDERMATOPHYTOSISLICHEN STRIATUS
PITYRIASIS ROSEAGUTTATE PARAPSORIASISDIGITATE DERMATOSISMILIARIA RUBRA
PITYRIASIS ALBAERYTHEMA ANNULARE CENTRIFUGMCHILD ACRAL PAPULAR ERUPTIONRUBIOLA
INCONTINENTIA PIGMENTIALLERGIC CONTACT DERMATITISARTHROPOD BITE OR STING
BULLOUS PEMPHIGOIDHERPES GESTATIONISPEMPHIGUS VULGARISERYTHEMA MULTIFORME
TOXIC EPIDERMAL NECROLYSISPHOTODERMATITISDERMATOMYOSITIS
DISCOID LUPUS ERYTHEMATOSUSDRUG-INDUCED ERUPTIONVIRAL EXANTHEM
ERYTHEMA DYSCHROMICUM PERSTANSLICHEN SCLEROSUS ET ATROPHICUSRADIODERMATITIS
POIKILODERMA CONGENITALEBULLOUS PEMPHIGOIDPITYRIASIS LICHENOIDES ACUTA
LYMPHOMATOID PAPULOSISGRAFT VERSUS HOST REACTIONLICHEN PLANUS
LICHEN PLANUS-LIKE KERATOSISDRUG-INDUCED ERUPTIONLICHENOID PURPURALICHEN AUREUS
PITYRIASIS LICHENOIDES CHRONICAPARAPSORIASIS EN PLAQUESPOIKILODERMA ATROPHICANS
DISSEMINATED POROKERATOSISLUPUS ERYTHEMATOSUSPIGMENTED PURPURIC DERMATOSI
GRAFT VERSUS HOST REACTIONSECONDARY SYPHILISLYMPHOMATOID PAPULOSIS
PIGMENTED PURPURIC DERMATITISVIRAL EXANTHEMERYTHEMA ANNULARE CENTRIFUGUM
TINEA VERSICOLORERYTHRASMAPEDICULOSISLYMPHOMATOID PAPULOSISRICKETTSIAL FEVER
ERYTHEMA MULTIFORMERHYTHMIC PARADOXIC ERUPTIONERYTHEMA DYSCHROMICUM PERSTS
URTICARIAINSECT BITE OR STINGPAPULAR DERMATITIS OF PREGNANCY
DRUG-INDUCED ERUPTIONERYTHEMA PERSTANSERYTHEMA MARGINATUM
ERYTHEMA ANNULAR CENTRIFUGUMALLERGIC REACTIONALOPECIA MUCINOSA
STAPH. FOLLICULAR KERATOSISFOLLICULAR MUCINOSISFOX-FORDYCE DISEASE
ECZEMATOUS DERMATITISLICHEN NITIDUSLICHEN SCROFULOSORUMSARCOIDOSISTUBERCULOSIS
TERTIARY SYPHILISBERYLLIUM GRANULOMAZIRCONIUM GRANULOMA
SARCOIDOSISTUBERCULOSISLEPROSYSYPHILISLEISHMANIASISBERYLLIUM GRANULOMAROSACEA
ZIRCONIUM GRANULOMASILICA GRANULOMAFOREIGN BODY GRANULOMA
WEGENER'S GRANULOMATOSISMYCOSIS FUNGOIDESPAGETOID RETICULOSISWORINGER-KOLOPP
SEZARY SYNDROMEHODGKINS'S DISEASEMYCOSIS FUNGOIDESMALIGNANT T-CELL LYMPHOMA
ALVEOLAR SOFT PART SARCOMAFIBROUS HISTIOCYTOMADERMATOFIBROMA

TABLE Ib

SEQUENTIAL DUMP OF

LIMBS.1

FILE TYPE IS INTERNAL

RECORD TYPE IS FIXED 34

```
00 = 01 31 01 33      (.1.3)
04 = 00 00 00 00      (....)
08 = 00 00 00 00      (....)
0C = 00 00 00 00      (....)
10 = 00 00 00 00      (....)
14 = 00 00 00 00      (....)
18 = 00 00 00 00      (....)
1C = 00 00 00 00      (....)
20 = 00 00            (..)

00 = 01 32 09 45      (.2.E)
04 = 50 49 44 45      (PIDE)
08 = 52 4D 41 4C      (RMAL)
0C = 00 00 00 00      (....)
10 = 00 00 00 00      (....)
14 = 00 00 00 00      (....)
18 = 00 00 00 00      (....)
1C = 00 00 00 00      (....)
20 = 00 00            (..`
```

```
00 = 01 33 06 44    (.3.D)
04 = 45 52 4D 41    (ERMA)
08 = 4C 00 00 00    (L...)
0C = 00 00 00 00    (....)
10 = 00 00 00 00    (....)
14 = 00 00 00 00    (....)
18 = 00 00 00 00    (....)
1C = 00 00 00 00    (....)
20 = 00 00          (..)

00 = 01 34 0C 53    (.4.S)
04 = 55 42 43 55    (UBCU)
08 = 54 41 4E 45    (TANE)
0C = 4F 55 53 00    (OUS.)
10 = 00 00 00 00    (....)
14 = 00 00 00 00    (....)
18 = 00 00 00 00    (....)
1C = 00 00 00 00    (....)
20 = 00 00          (..)

00 = 01 31 01 31    (.1.1)
04 = 00 00 00 00    (....)
08 = 00 00 00 00    (....)
0C = 00 00 00 00    (....)
10 = 00 00 00 00    (....)
14 = 00 00 00 00    (....)
18 = 00 00 00 00    (....)
1C = 00 00 00 00    (....)
20 = 00 00          (..)

00 = 01 34 0C 53    (.4.S)
04 = 55 42 43 55    (UBCU)
08 = 54 41 4E 45    (TANE)
0C = 4F 55 53 00    (OUS.)
10 = 00 00 00 00    (....)
14 = 00 00 00 00    (....)
18 = 00 00 00 00    (....)
1C = 00 00 00 00    (....)
20 = 00 00          (..)
```

TABLE II

```
100 !   DECISION TREE FILING PROGRAM
110 !   THIS PROGRAM ACCEPTS AND FILES DATA IN TWO-FIELD RECORDS.  THE
120 !   FIRST FIELD ACCEPTS ONE TO FOUR DIGITS.  THE SECOND FIELD
130 !   ACCEPTS MAXIMUM OF 28 ALPHANUMERIC CHARACTERS.

210 OPEN #1:"RS232.DA=8" ! THE CHANNEL TO THE PRINTER
220 DISPLAY "1 START NEW FILE,2 TO END"
230 CALL KEY(0,W,STATUS):: IF STATUS=0 THEN 230
240 ON W-48 GO TO 250,470
250 INPUT "NEW FILE # ?":FILE :: CALL CLEAR
260 DISPLAY AT(24,1):"NEW FILE";FILE
270 ACCEPT AT(24,10)SIZE(-3):FILE :: IF FILE=0 THEN 220
280 DISPLAY AT(24,1):"ANTECEDENT ";LF$
290 ACCEPT AT(24,12)SIZE(-3)VALIDATE(DIGIT):LF$
300 DISPLAY "FILE ";FILE;"ANTECEDENT ";LF$
310 PRINT #1:CHR$(14);"FILE ";FILE,"ANTECEDENT ";LF$
320 DD=1
330 OPEN #2:"DSK"&STR$(DD)&"."&STR$(FILE),OUTPUT,RELATIVE,INTERNAL,FIXED 34
340 TOTAL=1 :: PRINT 32,REC 0:LF$,TOTAL
370 DISPLAY AT(24,1):"NEXT RECORD FILE ";STR$(NRF)
380 ACCEPT AT(24,19)VALIDATE(DIGIT)SIZE(-4)BEEP:NRF$
390 DISPLAY NRF$: :: IF NRF$=" " OR NRF$="    "THEN NRF$=""
```

```
400 ACCEPT AT(24,1)SIZE(28)BEEP:TEXT$ :: IF TEXT$="" THEN 450
410 PRINT #2,REC TOTAL:NRF$,TEXT$ :: DISPLAY NRF$:TEXT$
420 IF NRF 999 THEN F$=SEG$(NRF$,1,3)!  THE FIRST THREE DIGITS WILL BE
    THE FILE NUMBER
425 REC$=SEG$(NRF$,4,1)!  THE FOURTH DIGIT WILL BE THE RECORD NUMBER
430 PRINT #1:CHR$(14);TAB(3);F$;TAB(7);REC$;TAB(9);TEXT$
440 NRF=NRF+1 :: TOTAL=TOTAL+1 :: GOTO 370
450 PRINT #2,REC 0:LF$,STR$(TOTAL-1)
460 PRINT #1 :: CLOSE #2 :: FILE=FILE+1 :: GOTO 260
470 CLOSE #1 :: STOP
```

TABLE III

```
100 ! INTERACTIVE COMPUTER-GENERATED DIFFERENTIAL DIAGNOSIS AND BIOPSY
    REPORT

120 !    VARIABLES:
130 !    D$() ....... ARRAY TO HOLD SELECTED DESCRIPTIVE PHRASES
140 !    DDX$()...... ARRAY TO HOLD SELECTED DIFFERENTIAL DIAGNOSES
150 !    INF$()...... ARRAY TO HOLD CLINICAL INFORMATION

180 !    DIMENSIONS:
190 OPTION BASE 1 :: DIM D$(12),DDX$(12),INF$(12)
200 CALL CLEAR :: DISPLAY "BIOREPORT": :
210 INPUT "NAME OF FACILITY ? ":PATH$
220 INPUT "STREET ADDRESS ? ":STRT$
230 INPUT "CITY STATE ZIP CODE ? ":CITY$
240 INPUT "TELEPHONE ? ":TEL$
260 FOR D=1 TO 12 :: D$(D),DDX$(D),INF$(D)="" :: NEXT D ! ARRAYS
    INITIALISED TO NULL STRINGS
270 PRINT "CONTINUE ? Y OR N "
280 CALL KEY(0,K,S):: IF S=0 THEN 280
300 FILE=1 :: D=1 :: REC$="" ! FIRST THREE DIGITS REPRESENT FILE NUMBER.
    FOURTH DIGIT REPRESENTS RECORD NUMBER
310 FIL$=STR$(FILE):: FILE$=SEG$(FIL$,1,3):: REC$=SEG$(FIL$,4,1)::
    FILE=VAL(FILE$)
320 DD=1
330 ON ERROR 2020
340 OPEN #2: "DSK"&STR$(DD)&"."STR$(FILE),RELATIVE,INTERNAL,FIXED 34
350 CALL CLEAR :: INPUT #2,REC 0:LF$,TOTAL$ ! NUMBER OF ANTECEDENT FILE
    AND THE TOTAL OF RECORDS IN CURRENT FILE
360 TOTAL=VAL(TOTAL$)
380 DISPLAY " 0 TO GO BACK"
390 FOR RCRD=1 TO TOTAL
400 INPUT #2:FILE$,TEXT$
410 DISPLAY RCRD:" ":TEXT$ :: NEXT RCRD
420 DISPLAY TOTAL+1;" TO MODIFY"
425 IF FILE$="" THEN 580
430 CALL KEY(0,K,S):: IF S=0 OR K=13 THEN 430 ! OPERATOR CHOOSES
    APPROPRIATE DESCRIPTIVE PHRASE
450 INPUT #2,REC K-48:FILE$,TEXT$
460 IF KEY-48=0 THEN 480 !       TO RETURN TO THE ANTECEDENT FILE
470 D$(D)=TEXT$ :: D=D+1 ! THE CHOSEN PHRASE IS STORED IN THE DESCRIPTIVE
    ARRAY
480 CLOSE #2 :: FILE=VAL(FILE$) ! MACHINE WILL OPEN THE FILE CODED WITH
    THE CHOSEN PHRASE
490 CALL CLEAR :: DISPLAY TEXT$ :: DISPLAY :: GO TO 310
580 DISPLAY A (24,1):"MOST LIKELY DIAGNOSIS" :: DISPLAY AT (24,27):REC$
    :: ACCEPT AT (24,27)SIZE(-2)BEEP:REC$
590 IF RE$="" THEN 580 ! NUMBER OF MOST LIKELY DIAGNOSIS WILL FLASH ON &
    OFF
600 IF REC$="0" THEN INPUT #2,REC 0:LF$,TEXT$ :: CLOSE #2 ::
    FILE=VAL(LF$):: GO TO 310
```

```
610 CHOICE=VAL(REC$) !           THE RECORD NUMBER OF THE FINAL DIAGNOSIS
630 INPUT #2,REC CHOICE:FILE$,INF$(1) !  THE DIAGNOSIS IS WRITTEN INTO
    THE INFORMATION ARRAY
650 PRINT "NAME OF PATIENT   ?  " :: ACCEPT SIZE(26):INF$(2)
690 PRINT "TO PRINT REPORT ? " :: DISPLAY AT(24,24):"Y"
700 ACCEPT AT(24,24)SIZE(-1):PRINT$ :: IF PRINT$   "Y" THEN CLOSE #2
    :: PRINT :: :: GOTO 260 ELSE D=1
750 FOR DX=1 to TOTAL
760 INPUT #2,REC DX:FILE$, TEXT$
770 DISPLAY DX;" "; TEXT$
780 DISPLAY AT(24,24):"Y"
790 ACCEPT AT(24,24)SIZE(-1):DX$
800 IF DX$   "Y" THEN 820
810 DDX$(D)=TEXT$ :: D=D+1 :: IF D 11 THEN 830
820 NEXT DX
830 INPUT "COMMENT ? ":INF$(12) ! OPTIONAL INFORMATION STORED IN ARRAY
840 INPUT "DATE OF BIOPSY ? ":INF$(4)
850 INPUT "AGE ? ":INF$(5)
860 INPUT "LAB NUMBER ? ":INF$(3)
870 INPUT "DURATION ? ":INF$(6)
880 INF$(7)=NL$ !                         THE NEXT ACCESSION NUMBER
890 PRINT "SITE ? " :: ACCEPT SIZE(26):INF$(8)
900 INPUT "TAKEN BY ? ":INF$(9)
910 INPUT "CLINICAL DIAGNOSIS ? ":INF$(10)
920 INPUT "DATE OF REPORT ? ":INF$(11)
930 !
940 CALL CLEAR ! PRINTING ALGORITHM
945 END
2020 DISPLAY "CHECK FILE"; FILE :: RETURN ! ERROR HANDLING
```

TABLE IV

BIOPSY REPORT

NAME OF PATIENT:                          DATE OF BIOPSY:

AGE:                                      LAB. NUMBER:

DURATION OF LESION:                       ACCESSION NO.:

SITE:                                     TAKEN BY:

CLINICAL DIAGNOSIS:

DERMATOLOGICAL PATHOLOGY

DESCRIPTION OF SECTION:

THE DIAGNOSTIC CHANGES ARE: DERMAL, ELASTOSIS,
IN THE PAPILLARY CORIUM, CONFLUENT DILATED PAPILLAE.

DIFFERENTIAL DIAGNOSIS:

ACTINIC ELASTOSIS
        CUTIS RHOMBOIDALIS
        ERYTHEMA AB IGNE
        COLLOID MILIUM

We claim:

1. An interactive coomputerized system for performing a differential dermatopathological diagnosis of a biopsy based on characteristics of said biopsy product, said system comprising
   an output means for presenting a set of plurality of selected histopathological changes to an operator;
   an input means for entering operator selected responses;
   a memory means for storing a hierarchical data base, said data base comprised of a plurality of downwardly linked files, each file comprised of a header record and a plurality of data records, said operator selected response corresponding to one of said data records, said header record comprised of a file identification field and a field for containing the number of the data records located in the file, and each said data record comprised of a linking identifier field and a data field, said data field containing a histopathological change when said identifier field contains an entry of a file identifier that points to a data record located below in the hierarchy and containing a differential diagnosis when said identifier field does not contain said file identifier; and
   processor means under a programmed control for receiving operator entered responses, for responding to the contents of the identifier field of said operator selected record for retrieving the linked file stored elsewhere in said memory means, and for providing the data stored in said linked file to said output means.

2. The interactive computerized differential diagnostic system as claimed in claim 1, wherein said header record of a present file also includes an antecedent linking identifier field for containing the identification of the file which had identified the present file.

3. The interactive computerized differential diagnostic system as claimed in claim 1, wherein said identifier field of a data record containing a differential diagnosis is empty; and wherein said processor means detects said empty field and provides an indication on said output means that the displayed data is diagnosis data.

4. The interactive computerized differential diagnostic system as claimed in claim 1, wherein said output means includes a printer; and wherein when said processor means detects that said indentifier field does not contain a file identifier, said processor means causes said printer to print a biopsy report containing the selected diagnostic changes and containing the differential diagnosis.

5. The interactive computerzied differential diagnostic system as claimed in claim 1, wherein said data record further includes a preferred diagnosis field which when filled contains the identification of a preferred diagnosis stored in said data field of the next downwardly linked file.

6. An interactive computerized system for performing a differential dermatopathological diagnosis of a biopsy based on characteristics of said biopsy product, said system comprising
   an output means for presenting a set of a plurality of selected histopathological changes to an operator;
   an input means for entering operator selected responses;
   a memory means for storing a hierarchical data base, said data base comprised of a plurality of downwardly linked files, each file comprised of a header record and a plurality of data records, said operator selected response corresponding to one of said data records, said header record comprised of a file identification field and each said data record comprised of a linking identifier field and a data field, said data field containing a histopathological change when said identifier field contains an entry of a file identifier that points to a data record located below in the hierarchy and containing a differential diagnosis when said identifier field does not contain said file identifier;
   processor means under a programmed control for receiving operator entered responses, for responding to the contents of the identifier field of said operator selected record for retrieving the linked file stored elsewhere in said memory means, and for providing the data stored in said linked file to said output means; and
   wherein said identifier field of a data record containing a differential diagnosis is empty and said processor means detects said empty field and provides an indication on said output means that the displayed data is diagnosis data.

7. The interactive computerized differential diagnostic system as claimed in claim 6, wherein said header record of a file also includes a field for containing the number of the data records located in the file.

8. The interactive computerzied differential diagnostic system as claimed in claim 6, wherein said header record of a present file also includes an antecedent linking identifier field for containing the identification of the file which had identified the present file.

9. The interactive computerized differential diagnostic system as claimed in claim 6, wherein said output means includes a printer; and wherein when said processor means detects that said identifier field does not contain a file identifier, said processor means causes said printer to print a biopsy report containing the selected diagnostic changes and containing the differential diagnosis.

10. The interactive computerized differential diagnostic system as claimed in claim 6, wherein said data record further includes a preferred diagnosis field which when filled contains the identification of a preferred diagnosis stored in said data field of the next downwardly linked file.

11. An interactive computerized system for performing a differential dermatopathological diagnosis of a biopsy based on characteristics of said biopsy product, said system comprising an output means for presenting a set of a plurality of selected histopathological changes to an operator;

an input means for entering operator selected responses;

a memory means for storing a hierarchical data base, said data base comprised of a plurality of downwardly linked files, each file comprised of a header record and a plurality of data records, said operator selected response corresponding to one of said data records, said header record comprised of a file identification field and each said data record comprised of a linking identifier field and a data field, said data field containing a histopathological change when said identifier field contains an entry of a file identifier that points to a data record located below in the hierarchy and containing a differential diagnosis when said identifier field does not contain said file identifier and said data field including a preferred diagnosis field which when filled contains the identification of a preferred diagnosis stored in said data field of the next downwardly linked file; and processor means under a programmed control for receiving operator entered responses, for responding to the contents of the identifier field of said operator selected record for retrieving the linked file stored elsewhere in said memory means, and for providing the data stored in said linked file to said output means.

12. The interactive computerized differential diagnostic system as claimed in claim 11, wherein said header record of a present file also includes an antecedent linking identifier field for containing the identification of the file which had identified the present file.

13. The interactive computerized differential diagnostic system as claimed in claim 11, wherein said output means includes a printer; and wherein when said processor means detects that said identifier field does not contain a file identifier, said processor means causes said printer to print a biopsy report containing the selected diagnostic changes and containing the differential diagnosis.

* * * * *